(12) United States Patent
Myllyoja et al.

(10) Patent No.: US 11,339,344 B2
(45) Date of Patent: May 24, 2022

(54) TIO₂ CATALYST IN KETONISATION REACTIONS TO PRODUCE RBO

(71) Applicant: Neste Oyj, Espoo (FI)

(72) Inventors: Jukka Myllyoja, Porvoo (FI); Sonja Kouva, Porvoo (FI); Jarno Kohonen, Porvoo (FI); Rami Piilola, Porvoo (FI); Mika Kettunen, Porvoo (FI); Jaana Makkonen, Porvoo (FI); Meri Hovi, Porvoo (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 16/623,276

(22) PCT Filed: Jun. 15, 2018

(86) PCT No.: PCT/EP2018/065971
§ 371 (c)(1),
(2) Date: Dec. 16, 2019

(87) PCT Pub. No.: WO2018/234186
PCT Pub. Date: Dec. 27, 2018

(65) Prior Publication Data
US 2020/0181503 A1 Jun. 11, 2020

(30) Foreign Application Priority Data

Jun. 19, 2017 (FI) ..................................... 20175569
Aug. 31, 2017 (FI) ..................................... 20175780
(Continued)

(51) Int. Cl.
*C10G 3/00* (2006.01)
*C07C 45/41* (2006.01)
(Continued)

(52) U.S. Cl.
CPC ........... *C10M 105/04* (2013.01); *B01D 3/143* (2013.01); *B01J 21/04* (2013.01); *B01J 21/063* (2013.01);
(Continued)

(58) Field of Classification Search
CPC .......... C10G 3/00; C10G 67/02; C07C 45/41; C07C 51/353; C07C 51/367; C11C 1/04; C10L 1/08; B01J 23/78
See application file for complete search history.

(56) References Cited

U.S. PATENT DOCUMENTS 8,679,805 B2 3/2014 Chung et al.
9,523,061 B2 12/2016 Nelson et al.
(Continued)

FOREIGN PATENT DOCUMENTS

CN 1867653 A 11/2006
CN 102300967 A 12/2011
(Continued)

OTHER PUBLICATIONS

Eisner, U. et al. "The synthesis of long-chain, branched, hydroxyaliphatic compounds", Bull. Soc. Chim. FR, pp. 212-218, 1995.
(Continued)

*Primary Examiner* — Youngsul Jeong
(74) *Attorney, Agent, or Firm* — Buchanan Ingersoll & Rooney PC

(57) ABSTRACT

A method for producing a renewable base oil from a feedstock of biological origin includes providing a feedstock, the feedstock including: 2-95 wt % of a mixture of free fatty acids; 5-98 wt % fatty acid glycerols selected from mono-glycerides, di-glycerides and tri-glycerides of fatty acids; 0-50 wt % of one or more compounds selected from the list consisting of: fatty acid esters of the non-glycerol type, fatty amides and fatty alcohols; a major part of the feedstock being a mixture of free fatty acids and fatty acid glycerols; subjecting all or part of the feedstock to ketonisation reaction conditions where two free fatty acids react to yield a ketone stream, and subjecting the ketone stream to both hydrodeoxygenation and to hydroisomerisation reac-
(Continued)

tion conditions, to yield a deoxygenated and isomerised base oil product stream containing the renewable base oil.

30 Claims, 2 Drawing Sheets

(30) Foreign Application Priority Data

| Aug. 31, 2017 | (FI) | ................................. 20175781 |
|---|---|---|
| Aug. 31, 2017 | (FI) | ................................. 20175782 |
| Dec. 7, 2017 | (FI) | ................................. 20176095 |

(51) Int. Cl.

| C10M 105/04 | (2006.01) |
|---|---|
| B01J 21/04 | (2006.01) |
| B01J 21/06 | (2006.01) |
| B01J 23/883 | (2006.01) |
| B01J 35/10 | (2006.01) |
| C10G 45/58 | (2006.01) |
| C10L 1/08 | (2006.01) |
| B01J 29/85 | (2006.01) |
| C10G 67/02 | (2006.01) |
| C11C 1/04 | (2006.01) |
| C10M 105/06 | (2006.01) |
| C10M 169/04 | (2006.01) |
| B01D 3/14 | (2006.01) |
| C07C 51/44 | (2006.01) |
| C10M 177/00 | (2006.01) |
| C11C 1/10 | (2006.01) |
| C10N 30/00 | (2006.01) |
| C10N 20/00 | (2006.01) |
| C10N 30/02 | (2006.01) |
| C10N 30/04 | (2006.01) |
| C10N 30/10 | (2006.01) |
| C10N 30/12 | (2006.01) |
| C10N 30/14 | (2006.01) |
| C10N 30/16 | (2006.01) |
| C10N 70/00 | (2006.01) |

(52) U.S. Cl.
CPC ............ *B01J 23/883* (2013.01); *B01J 29/85* (2013.01); *B01J 35/1014* (2013.01); *B01J 35/1019* (2013.01); *B01J 35/1038* (2013.01); *B01J 35/1061* (2013.01); *C07C 45/41* (2013.01); *C07C 51/44* (2013.01); *C10G 3/46* (2013.01); *C10G 3/49* (2013.01); *C10G 3/50* (2013.01); *C10G 45/58* (2013.01); *C10G 67/02* (2013.01); *C10L 1/08* (2013.01); *C10M 105/06* (2013.01); *C10M 169/04* (2013.01); *C10M 177/00* (2013.01); *C11C 1/04* (2013.01); *C11C 1/10* (2013.01); *C10G 3/44* (2013.01); *C10G 2300/1003* (2013.01); *C10G 2300/1014* (2013.01); *C10G 2300/1018* (2013.01); *C10G 2300/202* (2013.01); *C10G 2300/301* (2013.01); *C10G 2300/302* (2013.01); *C10G 2300/304* (2013.01); *C10G 2300/308* (2013.01); *C10G 2300/4006* (2013.01); *C10G 2300/4012* (2013.01); *C10G 2300/4018* (2013.01); *C10G 2400/04* (2013.01); *C10G 2400/10* (2013.01); *C10L 2200/0484* (2013.01); *C10L 2270/026* (2013.01); *C10L 2290/543* (2013.01); *C10M 2203/022* (2013.01); *C10M 2203/0206* (2013.01); *C10M 2203/045* (2013.01); *C10M 2203/065* (2013.01); *C10N 2020/065* (2020.05); *C10N 2020/067* (2020.05); *C10N 2030/02* (2013.01); *C10N 2030/04* (2013.01); *C10N 2030/10* (2013.01); *C10N 2030/12* (2013.01); *C10N 2030/14* (2013.01); *C10N 2030/16* (2013.01); *C10N 2030/43* (2020.05); *C10N 2030/74* (2020.05); *C10N 2070/00* (2013.01)

(56) References Cited

U.S. PATENT DOCUMENTS

| 2005/0077208 | A1 | 4/2005 | Miller et al. |
|---|---|---|---|
| 2005/0263435 | A1 | 12/2005 | Skledar et al. |
| 2007/0135663 | A1 | 6/2007 | Aalto et al. |
| 2007/0161832 | A1 | 7/2007 | Myllyoja et al. |
| 2007/0244018 | A1 | 10/2007 | Visger et al. |
| 2008/0034645 | A1 | 2/2008 | Bressler |
| 2009/0014354 | A1 | 1/2009 | Knuuttila et al. |
| 2010/0234654 | A1 | 9/2010 | Wang et al. |
| 2011/0107656 | A1 | 5/2011 | Miller |
| 2012/0220506 | A1 | 8/2012 | Qin et al. |
| 2013/0190544 | A1 | 7/2013 | Wang et al. |
| 2013/0217606 | A1 | 8/2013 | Wang et al. |
| 2014/0046104 | A1 | 2/2014 | Mcneff et al. |
| 2014/0115955 | A1 | 5/2014 | Mcneff et al. |
| 2014/0171703 | A1 | 6/2014 | Wang et al. |
| 2014/0323665 | A1 | 10/2014 | Wu et al. |
| 2014/0335586 | A1 | 11/2014 | Zhang et al. |
| 2015/0018581 | A1 | 1/2015 | Kettunen et al. |
| 2015/0018588 | A1 | 1/2015 | Myllyoja et al. |
| 2015/0183915 | A1 | 7/2015 | Johnson et al. |
| 2015/0251168 | A1 | 9/2015 | Kettunen et al. |
| 2016/0137944 | A1 | 5/2016 | Liang et al. |
| 2017/0088789 | A1 | 3/2017 | Grisso et al. |
| 2017/0240832 | A1 | 8/2017 | Hahn et al. |
| 2017/0334806 | A1 | 11/2017 | Agee |
| 2017/0362154 | A1 | 12/2017 | Kettunen et al. |
| 2018/0171252 | A1 | 6/2018 | Fourage et al. |
| 2020/0181504 | A1 | 6/2020 | Myllyoja et al. |
| 2020/0181527 | A1 | 6/2020 | Kulmala et al. |
| 2021/0139786 | A1 | 5/2021 | Toppinen et al. |
| 2021/0139787 | A1 | 5/2021 | Myllyoja et al. |

FOREIGN PATENT DOCUMENTS

| CN | 102906229 A | 1/2013 | | |
|---|---|---|---|---|
| CN | 103773442 A | 5/2014 | | |
| DE | 102009017827 A1 | 10/2010 | | |
| DK | 2809745 A1 | 12/2014 | | |
| EP | 1741767 A1 | 1/2007 | | |
| EP | 1741768 A1 | 1/2007 | | |
| EP | 1741767 B1 | 7/2015 | | |
| EP | 1741767 B1 * | 7/2015 | ............ | C10G 45/08 |
| EP | 2809745 B1 | 4/2016 | | |
| EP | 3012310 A1 | 4/2016 | | |
| JP | 2004124080 A | 4/2004 | | |
| WO | 00/68799 A1 | 11/2000 | | |
| WO | 2007061698 A2 | 5/2007 | | |
| WO | 2007068795 A1 | 6/2007 | | |
| WO | 2007068800 A2 | 6/2007 | | |
| WO | 2008152200 A1 | 12/2008 | | |
| WO | 2012156679 A1 | 11/2012 | | |
| WO | 2013113976 A1 | 8/2013 | | |
| WO | 2014099371 A2 | 6/2014 | | |
| WO | 2014099373 A1 | 6/2014 | | |
| WO | 2016061050 A1 | 4/2016 | | |
| WO | 2016062868 A1 | 4/2016 | | |
| WO | WO-2016062868 A1 * | 4/2016 | .......... | C10G 65/043 |
| WO | 2017001606 A1 | 1/2017 | | |

OTHER PUBLICATIONS

Rush, D. et al. "Generation of unusual branched long chain alkanes from hydrous pyrolysis of anamox bacterial biomass", Organic Geochemistry, vol. 76, pp. 136-145, 2014.

(56) References Cited

OTHER PUBLICATIONS

Tamai, Y. et al. "Estimation of flow activation volume of synthetic ester lubricants", J. Japan Petrol. Inst., vol. 25, No. 5, pp. 281-285, 1982.

Toubiana, R. et al. "Long-chain aliphatic substances reltaed to bacterial lipids" in Ann. Chim., Paris, FR: 1962, vol. 7, pp. 593-642.

International Search Report (PCT/ISA/210) dated Jul. 19, 2018, by the European Patent Office as the International Searching Authority for International Application No. PCT/EP2018/065971.

International Preliminary Report on Patentability (Chapter of the Patent Cooperation Treaty) (PCT Rule 44bis) (Form PCT/IB/373) dated Dec. 24, 2019 and the Written Opinion of the International Searching Authority (Form PCT/ISA/237) dated Jul. 19, 2018, in the corresponding International Application No. PCT/EP2018/065971 (7 pages).

International Search Report (PCT/ISA/210) dated Jul. 19, 2018, by the European Patent Office as the International Searching Authority for International Application No. PCT/EP2018/065973.

International Preliminary Report on Patentability (Chapter of the Patent Cooperation Treaty) (PCT Rule 44bis) (Form PCT/IB/373) dated Dec. 24, 2019 and the Written Opinion of the International Searching Authority (Form PCT/ISA/237) dated Jul. 19, 2018, in the corresponding International Application No. PCT/EP2018/065973. (6 pages).

Office Action dated Jan. 6, 2021, by the U.S. Patent and Trademark Office in U.S. Appl. No. 16/623,306.

Deffense Etienne, "From Organic Chemistry to Fat and Oil Chemistry", OCL, vol. 16, No. 1, 2009, pp. 14-24.

International Search Report (PCT/ISA/210) and Written Opinion (PCT/ISA/237) received for PCT Application No. PCT/EP2018/065976, dated Aug. 27, 2018, 11 pages.

International Search Report (PCT/ISA/210) and Written Opinion (PCT/ISA/237) received for PCT Application No. PCT/EP2018/065978, dated Sep. 13, 2018, 16 pages.

International Search Report (PCT/ISA/210) and Written Opinion (PCT/ISA/237) received for PCT Application No. PCT/EP2018/065980, dated Jul. 25, 2018, 10 pages.

Non Final Office Action dated Mar. 31, 2021, by the U.S. Patent and Trademark Office in U.S. Appl. No. 16/623,188, 10 pages.

Non Final Office Action dated Nov. 5, 2020, by the U.S. Patent and Trademark Office in U.S. Appl. No. 16/623,257, 8 pages.

First Office Action dated Jul. 2, 2021, by the Chinese Patent Office in corresponding Chinese Patent Application No. 201880039835.4, and an English Translation of the Office Action. (7 pages).

Notice of Allowance dated Jun. 18, 2021, by the U.S. Patent and Trademark Office in U.S. Appl. No. 16/623,210.

Notice of Allowance dated Jul. 6, 2021, by the U.S. Patent and Trademark Office in U.S. Appl. No. 16/623,306.

Notice of Allowance dated Jul. 12, 2021, by the U.S. Patent and Trademark Office in U.S. Appl. No. 16/623,188.

Notice of Allowance dated Jul. 15, 2021, by the U.S. Patent and Trademark Office in U.S. Appl. No. 16/623,257.

* cited by examiner

Figure 1 – Scheme for Renewable base oil production
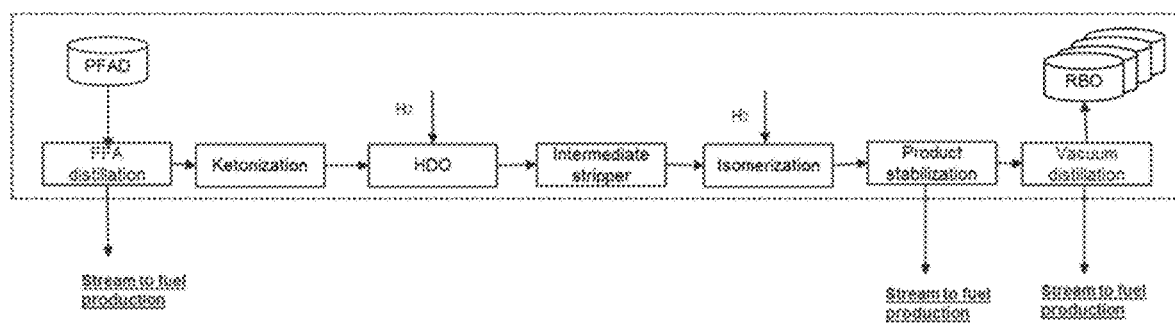
Figure 2 – Scheme for Renewable base oil, diesel and naphtha production
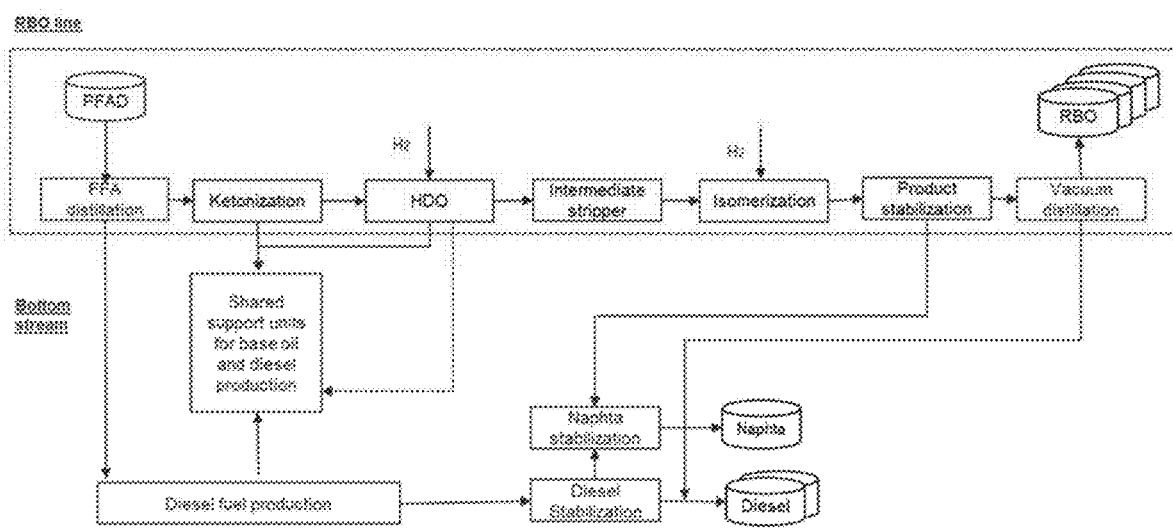

Figure 3 – Scheme for Renewable base oil, diesel and naphtha production
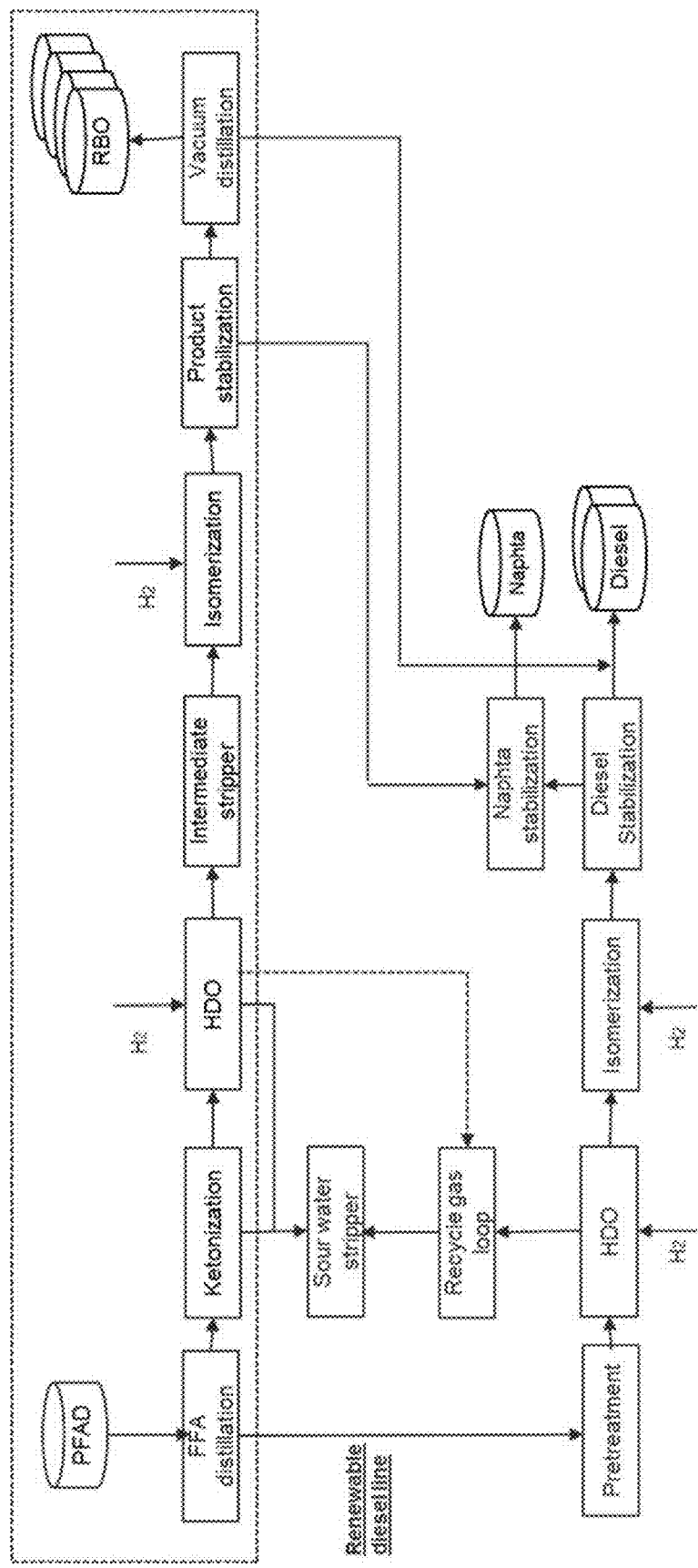

TIO$_2$ CATALYST IN KETONISATION REACTIONS TO PRODUCE RBO

TECHNICAL FIELD

The present invention relates to the field of hydrotreatment of biological oil, in particular to methods for producing renewable base oil and diesel oil, such as methods for producing renewable base oil, diesel oil and naphtha, in a process efficient manner. The invention focuses on the use of a specific ketonisation catalyst with increased life time and its impact on side production of heavies and the life time of the hydrooxygenation catalyst.

BACKGROUND ART

The technology relating to hydrotreatment of biological oils, such as plant oils and animal fats, has received much attention since the combined steps of hydrodeoxygenation and hydroisomerisation of plant oils was first found to result in a renewable diesel with improved cold flow properties back in the last years of the 20th century. In the beginning of the 21th century the manufacture of renewable base oil has also been investigated through a number of routes, including double-bond oligomerisation of renewable oils or ketonisation reactions of fatty acids.

The hydrotreatment of biological oils are for the most part catalysed. Catalytic hydrotreatment of biological oils on an industrial scale (>100 kt biological oil annually) faces several challenges, such as the time that the plant or reactor can remain on-stream before maintenance is required. One of the causes for reduced times on-stream is the deactivation of the catalyst, or the physical plugging of the catalyst bed, causing an increased and undesired pressure drop. The catalyst life time is highly dependent on the quality of the feedstock. One of the challenges of catalytic hydrotreatment is the catalyst life time in particular in combination with the processing of more degraded feeds comprising glycerides together with certain amounts of more reactive free fatty acids (FFA), compared to less degraded biological oils, such as for example edible rapeseed oil, which has very low amounts of free fatty acids. Another challenge in the hydrotreatment of biological oils is to reduce the overall hydrogen amount needed to convert the biological oil to renewable diesel or to renewable base oil.

EP 1 741 768 (to Neste Oyj) provides a solution to the undesired side reactions in the manufacture of diesel starting from a biological oil having more than 5 wt % free fatty acids. It was found that diluting the free fatty acid containing feed with a large amount of hydrocarbon diluting agent reduced the undesired side reactions, allowing for improved catalyst life time and thus more time on-stream.

There is a desire to use renewable oils that cannot be used for human consumption. The biological oils used for processing into renewable diesel and renewable base oils continues to become more and more degraded as well as more complex compared to examples of pure triglyceride feeds sometimes given in the prior art. Accordingly, there is a need in the art for processes that can utilise such degraded and complex biological oils or mixtures thereof that contain varying amounts of free fatty acids, in particular for the preparation of renewable diesel and renewable base oil.

WO 2007/068795 A1 (to Neste Oil Oyj) describes (see e.g. FIG. 1 of that application) a complex feed, which is diluted with hydrocarbons, and processed by prehydrogenation, ketonisation, hydrodeoxygenation, stripping, hydroisomerisation, optional hydrofinishing, and distillation into a renewable base oil, renewable diesel as well as a renewable gasoline. The reactions are carried out under conditions which include the use of catalysts for the different process steps. In the ketonisation step (see page 24 of that application) metal oxide catalysts may be used, typically metals include Na, Mg, K, Ca, Mn, Ni, Al, etc., such as MnO$_2$ or the double metal oxide NiMo/Al$_2$O$_3$. Other examples from prior art is CaO, MnO and MgO.

WO 2016/062868 A1 (to Neste Oil Oyj) describes a method of ketonisation wherein the ketonisation reaction applied is carried out under gas pressure directly on a feedstock, which preferably is in liquid form, and in the presence of a double catalyst selected as K$_2$O/TiO$_2$ as the sole catalyst being present during the ketonisation reaction.

There is still a need for more efficient processes that can process low-value biological oils containing free fatty acids and fatty acid esters into renewable base oils and renewable diesel, and in particular in an manner that improves e.g. the catalysts life time and results in complete conversion of the fatty acids with a minimum by-production of unwanted heavies.

SUMMARY OF THE INVENTION

The present invention was made in view of the prior art described above, and the object of the present invention is to provide a more efficient processing method of renewable oils having a certain amount of free fatty acids.

Another object of the invention is to provide a more efficient processing method which makes use of a particular ketonisation catalyst which secures a nearly complete conversion into the final product while at the same time minimises the production of fatty acid trimers (heavies) and improves the life time of the catalysts involved in the overall process.

Accordingly, the present invention in a first aspect provides a method for producing a renewable base oil from a feedstock of biological origin, the method comprising:

a) providing a feedstock, the feedstock comprising 2-95 wt % of a mixture of free fatty acids; 5-98 wt % fatty acid glycerols selected from mono-glycerides, di-glycerides and tri-glycerides of fatty acids; 0-50 wt % of one or more compounds selected from the list consisting of: fatty acid esters of the non-glycerol type, fatty amides and fatty alcohols; the major part of the feedstock being the mixture of free fatty acids and fatty acid glycerols;

b) subjecting all or part of the feedstock to ketonisation reaction conditions in the presence of a ketonisation catalyst selected as metal oxide catalyst comprising essentially titanium as metal, and where two free fatty acids react to yield a ketone stream, the ketone stream comprising as the major part saturated ketones, and c) subjecting the ketone stream to both hydrodeoxygenation reaction conditions and to hydroisomerisation reaction conditions, simultaneously or in sequence, to yield a deoxygenated and isomerised base oil product stream comprising the renewable base oil.

In connection with the present invention, a ketonisation catalyst selected as metal oxide catalyst comprising essentially titanium as metal is a catalyst, wherein titanium is not included in any combined, such as double, catalyst system, e.g. with other metals or metal oxides. However, traces of other metal may be present in amounts of 0.05-0.1 wt % or less. In particular, the catalyst comprises 0.05 wt % potassium or less.

Thus, according to the present invention all the feedstock or part of it is subjected to the ketonisation reaction using conditions wherein the ketonisation catalyst is selected as a metal oxide catalyst comprising essentially titanium as metal, and in particular selected as $TiO_2$, optionally on a support.

The ketonisation reaction of a fatty acid feed has typically been carried out under ketonisation conditions in the presence of various metal oxide catalysts, such as CaO, MnO, or MgO or double metal oxides like $K_2O/TiO_2$. However, an important disadvantage of these ketonisation catalysts is metal leaching, which is observed in the base oil stream and water. Due to this phenomenon, the ketone product stream has to be purified before being subjected to the hydrodeoxygenation reaction which follows the ketonisation step. Ionic exchange resin treatment or other purification treatment is normally applied for this purification. This implies that an additional, and expensive, purification step is required.

$K_2O/TiO_2$ is a particular example of a catalyst which has been applied as a useful ketonisation catalyst; however, leaching of some potassium has been observed during the first 3 to 4 weeks from startup of the plant. This challenges the subsequent hydrodeoxygenation of the ketone stream, because leaching of merely 2% potassium or more seriously damages the hydrodeoxygenation catalyst.

The present inventors have surprisingly found that a metal oxide catalyst comprising essentially titanium as the metal, in particular $TiO_2$, is very active in fatty acid ketonisation and have high selectivity, and it is therefore anticipated that this catalyst type would be the one that could provide the most efficient renewable base oil production. The use of this $Ti_2O$ catalyst for ketonisation has not been published in the literature in connection with the production of renewable base oil.

The catalyst allows almost complete conversion (>99.5%) of the free fatty acids into ketones, whereas at the same time the formation of unwanted fatty acid trimers (heavies) are minimized to a level of 2.5% or less.

Another advantage of using the metal oxide catalyst comprising essentially titanium as the metal is in that the catalyst does not leach metals during the catalyst' start up. The catalyst has good long term stability and do not form fines during ketonisation i.e. no decomposition of catalyst has been detected. The catalyst has excellent activity and selectivity compared to ketonisation published in the literature.

Thus, there are at least three observed advantages related to the metal oxide catalyst comprising essentially titanium as the metal, in particular the $Ti_2O$ catalyst: First, the ketonisation step shows highly selective conversion (99.5% or more) of the fatty acids into ketones and at the same time formation of 2.5% fatty acid trimers or less, whereby the subsequent hydrodeoxygenation can be conducted at milder reaction conditions. Second, substantially no metal leaching is observed during the start-up of the fatty acid ketonisation; metal leaching from the ketonisation catalyst, in particular in the first 3-4 weeks, is important for and will influence negatively the life time of the subsequent hydrodeoxygenation catalyst. Metal leaching will increase the fouling of the reactor and increase the pressure drop of the catalyst bed (plugging of the catalyst bed) and also deactivate the hydrodeoxygenation catalyst, thus the life time of this catalyst is significantly improved. For example every ppms of impurity in feed of commercial production unit means over 21 kg metals/month, over 250 kg/year (30 tons feed rate), which stays on the top of the catalyst bed and eventually plug the reactor. And third, the $Ti_2O$ catalyst is not decomposed during the ketonisation step, thus the catalyst life time is improved.

The inventors of the present invention has also found that a feedstock of degraded low-value biological oils containing free fatty acids and fatty acid esters can be processed into a renewable base oil and a renewable diesel oil in an efficient manner by first separating at least part of the free fatty acids from the feedstock and then processing this enriched free acid feed separately in a ketonisation reaction followed by hydrodeoxygenation and hydroisomerisation reactions to yield a renewable base oil stream. The remaining free fatty acid depleted feed can be processed in a separate hydrodeoxygenation and hydroisomerisation step to yield a renewable diesel fuel stream.

Separating the feedstock into two separate streams provides surprising advantages compared to a combined treatment of the entire feedstock, in that the ketonisation reaction of the separated feed having mainly free fatty acids may be run under conditions that result in almost complete (>90%, >95%, >99% or even ≥99.5%) conversion of the free fatty acids into ketones, as there is less undesired oligomerisation reaction compared to ketonisation of the entire stream. This ketone stream may be converted under milder hydrodeoxygenation conditions into the corresponding paraffins, compared to a feed that also comprise unconverted fatty acids or triglycerides. As an additional advantage, the fatty acid depleted feed will contain less of the free fatty acids compared to the (initial) feedstock and therefore use less hydrogen compared to the hydrogenation of the entire feedstock. This results in less overall hydrogen consumption due to the ketonisation reaction of the separate free fatty acid feed, because during ketonisation, 75% of the oxygen content of the fatty acids is removed as $CO_2$ and $H_2O$ without consuming hydrogen, and consequently that less hydrogen is required to convert the ketone stream.

The separation of the feed results in less overall hydrogen consumption, milder hydrodeoxygenation conditions for the ketone stream, when complete ketonisation conversion can be achieved, i.e. no unconverted fattyacids which needs more severe reaction conditions. Fatty acids are also very corrosive and might produce side reactions during HDO. Therefore a longer time on-stream for the reactor comprising the hydrodeoxygenation catalyst can be achieved, because it is exposed to less of the free fatty acids compared to a hydrotreatment of the same feed that has not undergone any prior separation.

Accordingly, the present invention in one embodiment of its first aspect provides a method, wherein the method further comprises producing a diesel fuel from the feedstock of biological origin, the method comprising after step a) that the feedstock is separated into at least the following two feeds:

a1) a free fatty acid enriched feed having a higher concentration of free fatty acids than the feedstock, the free fatty acids comprising $C_{10}$-$C_{24}$ fatty acids, preferably $C_{14}$-$C_{22}$, such as $C_{14}$, $C_{16}$, $C_{18}$, $C_{20}$ and $C_{22}$ fatty acids; and a2) one or more free fatty acid depleted feed(s) having higher concentration of the compounds selected from monoglycerides, di-glycerides and tri-glycerides of fatty acids, and having a higher boiling point than the free fatty acid feed;

b) subjecting the free fatty acid enriched feed to ketonisation reaction conditions in the presence of a ketonisation catalyst selected as metal oxide catalyst comprising essentially titanium as metal, and where two free fatty acids react to yield a ketone stream, the ketone stream comprising as the major part saturated ketones, and c) subjecting the ketone stream to both hydrodeoxygenation reaction conditions and to hydroisomerisation reaction conditions, simultaneously or in sequence, to yield a deoxygenated and isomerised base oil product stream comprising the renewable base oil; and e) transforming the one or more free fatty acid depleted feed(s) into a diesel product, preferably by subjecting the one or more free fatty acid depleted feed(s) to both hydrodeoxygenation reaction conditions and to hydroisomerisation reaction conditions, simultaneously or in sequence, to yield a deoxygenated and isomerised diesel product stream comprising the diesel fuel.

In accordance with the observations in relating to reduced metal leaching from the presently used ketonisation catalyst and metal leaching's influence on the activity and life time of the hydrooxygenation catalyst, the invention also provides in its second aspect the use of a ketonisation catalyst selected as a metal oxide catalyst comprising essentially titanium as the metal, such as $TiO_2$, for improving the catalyst life time of a hydrodeoxygenation catalyst in a plant for producing renewable base oil and/or diesel fuel, the plant comprising a fatty acid ketonisation stage comprising the ketonisation catalyst; the plant further comprising a hydrodeoxygenation stage comprising a hydrodeoxygenation catalyst; the hydrodeoxygenation stage being downstream of the ketonisation stage.

Some Definitions

The renewable base oil in the context of the present invention is derived from ketonisation of fatty acids. Being base oil, it boils within a base oil boiling range, such as above 380° C.

Renewable base oil in the context of the present invention is to be understood as a base oil being obtained from one or more renewable sources. Base oil is a well-known term, and base oil in the context of the present invention can be defined as a hydrocarbon based composition with a viscosity index above 80, for example the base oil in the context of the present invention can be even further defined as fulfilling the requirements of the API (The American Petroleum Institute) base oil groups I, II or III, preferably API group III.

The base oil affects many parameters of their endproducts or application such as the viscosity, oxidation stability, volatility, cold flow properties such as pour point, and viscosity index.

Base oils which can be manufactured from ketones obtained according to the present invention fulfil the requirement of Group III of The American Petroleum Institute which divides base oils into five main groups. Groups I to III are petroleum base oil of varying qualities.

TABLE 1

API base stock categories

| Group | Sulfur, wt-% | | Saturates, % | Viscosity Index (VI) |
|---|---|---|---|---|
| I | >0.03 | and/or | <90 | 80-119 |
| II | ≤0.03 | and | ≥90 | 80-119 |
| III | ≤0.03 | and | ≥90 | ≥120 |
| IV | Synthetic poly-alpha-olefins (PAOs) | | | |
| V | Any other type of base oil than group I-IV | | | |

A renewable diesel fuel is a hydrocarbon diesel product as opposed to e.g. oxygen-containing biodiesel, which are mono-alkyl fatty acid esters of biological oils. Being a diesel fuel, it boils within a diesel boiling range.

Common to the renewable base oil, diesel or naphtha are that they may be highly paraffinic, whereas the content of aromatics and/or oxygenates may be very low, such as below 0.5 vol %.

The renewable content may be determined from the starting materials, as well as being determined in the products by isotopic distribution involving $^{14}C$, $^{13}C$ and/or $^{12}C$ as described in ASTM D6866. Reference is made to WO 200/068799, which is hereby incorporated by reference. For example, typical $^{14}C$ isotope content of the total carbon content in the product, which is completely of biological origin, is at least 100%. Accordingly, a renewable base oil made from a feedstock of biological origin will be at least 100%.

The term fatty acid is well-known to the skilled person, and have been used to characterise a carboxylic acid consisting of a hydrocarbon chain and a terminal carboxyl group, in particular any of those carboxylic acids occurring as esters in fats and oils.

Feedstock

In the context of the present invention the feedstock comprises as the major part a mixture of free fatty acids and fatty acid esters, such as fatty acid glycerols. This is because the ketonisation reaction requires free fatty acids and because degraded or low-value biological oils are typically mixtures of free fatty acids and fatty acid glycerols, such as triglycerides or partial glycerides. The major part of the free fatty acids and fatty acid esters may, for example, be considered to be more than 50 wt %, such as more than 70 wt %, more than 90 wt %.

In degraded biological oil, part of the triglycerides, which can be used as high-value edible oils have been degraded to free fatty acids and partial glycerides, such as mono- and di-glycerides. The low-value biological oils may therefore have a higher amount of free fatty acids compared to the glyceride content (combined amount of mono-, di- and tri-glycerides). For example, in the refining of crude palm oil, a palm oil stripper may be used to separate crude palm oil into high-value edible palm oil and low-value palm oil fatty acid distillate (PFAD). The low-value PFAD is not fit for human consumption, and may advantageously be used in the methods according to the present invention.

BRIEF DESCRIPTION OF THE DRAWINGS

FIG. 1 shows a schematic overview of renewable base oil, diesel and naphtha production.

FIG. 2 shows a schematic overview of renewable base oil production, with additional shared support units for base oil and diesel production, for example in the form of sour water stripper and recycle gas loop, as well as optional naphtha and/or diesel production.

FIG. 3 shows a schematic overview of an integrated renewable base oil, diesel and naphtha production, with additional and optional sour water stripper and recycle gas loop.

DETAILED DESCRIPTION OF THE INVENTION

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose.

The invention in its first aspect relating to the method of claim 1 in particular relates to the following embodiments, taken alone or in combination with any one of the other embodiments mentioned herein:

The ketonisation catalyst may be $TiO_2$, optionally on a support.

The ketonisation catalyst may be in a form, where the content of the elements manganese, magnesium, calcium, and potassium are each below 0.05 wt % compared to the total catalyst weight as measured using x-ray diffraction. In particular the content of potassium is below 0.05 wt %.

The $TiO_2$ ketonisation catalyst may be in anatase form having an average pore diameter of 80-160 Å, and/or a BET area of 20-140 $m^2/g$, and/or porosity of 0.1-0.3 $cm^3/g$.

The method may further include a step wherein the deoxygenated and isomerised base oil product stream comprising the renewable base oil is distilled to obtain distilled renewable base oil.

The method may further include a step wherein a deoxygenated and isomerised product stream comprising the fuel oil is distilled to obtain distilled diesel fuel.

The method may additionally be for producing a naphtha fuel, where the naphtha fuel is obtained from distillation of both the deoxygenated and isomerised base oil product stream comprising the renewable base oil and from the distillation of a deoxygenated and isomerised diesel product stream comprising the diesel fuel.

Prior to step a) of the method, an initial feedstock comprising fatty acid esters may be pre-treated in at least a hydrolysis step thereby producing the feedstock, where the ratio of free fatty acids to fatty acid esters has been increased compared to the initial feedstock.

In certain variants, no pre-treatment by hydrogenation or by hydrolysis may be done in step a) or steps in-between steps steps a) to c).

When the hydrodeoxygenation and hydroisomerisation take place in sequence, in-between the hydrodeoxygenation and hydroisomerisation there may be a stripping step, where gasses are separated from liquids. This may occur in a high temperature and high pressure separation step, for example at a temperature in the range from 300 to 330° C. and a pressure in the range from 40 to 50 barg.

Prior to the optional distillation step of the deoxygenated and isomerised base oil product stream comprising the renewable base oil there may be a stripping step, where gasses are separated from liquids. This may be done at a temperature in the range of 320 to 350° C. and a pressure in the range of 3 to 6 barg.

The major part of the feedstock may be saturated free fatty acids.

The major part of the feedstock may be $C_{16}$ fatty acids.

The feedstock may be palm oil fatty acid distillate (PFAD).

The ketonisation reaction conditions may comprise one or more of the following: a temperature in the range from 300 to 400° C.; a pressure in the range from 5 to 30 barg; a WHSV in the range from 0.25 to 3 $h^{-1}$. The ketonisation reaction is in the presence of the ketonisation catalyst, the ketonisation catalyst being selected as a metal oxide catalyst comprising essentially titanium as metal. The ketonisation reaction may be in the presence of a gas in the range from 0.1 to 1.5 gas/feed ratio (w/w), the gas being selected from one or more of: $CO_2$, $H_2$, $N_2$, $CH_4$, $H_2O$.

The ketonisation reaction conditions may be selected such as to ensure liquid phase ketonisation.

The ketonisation catalyst may be $TiO_2$, and the content of metal impurities in the feedstock or the free fatty acid enriched feed immediately before it is subjected to the ketonisation reaction conditions and in the ketone stream obtained immediately after it has been subjected to the ketonisation reaction conditions may comprise at most 20 ppm manganese, at most 20 ppm magnesium, at most 20 ppm calcium, at most 20 ppm potassium, measured using inductively coupled plasma (ICP) metal analysis.

The ketone stream obtained immediately after it has been subjected to the ketonisation reaction conditions may comprise at most 5 ppm manganese, at most 5 ppm magnesium, at most 5 ppm calcium, at most 5 ppm potassium, measured using inductively coupled plasma (ICP) metal analysis.

The ketone stream obtained immediately after it has been subjected to the ketonisation reaction conditions may comprise at most 3 ppm manganese, at most 3 ppm magnesium, at most 3 ppm calcium, at most 3 ppm potassium, measured using inductively coupled plasma (ICP) metal analysis.

The hydrodeoxygenation reaction conditions may comprise one or more of the following: a temperature in the range from 250 to 400° C.; a pressure in the range from 20 to 80 barg; a WHSV in the range from 0.5 to 3 $h^{-1}$; and a $H_2$ flow of 350 to 900 nl $H_2$/l feed. The hydrodeoxygenation reaction may be performed in the presence of a hydrodeoxygenation catalyst, such as NiMo on an alumina support.

The isomerisation reaction conditions may comprise one or more of the following: a temperature in the range from 250 to 400° C.; a pressure in the range from 10 to 60 barg; a WHSV in the range from 0.5 to 3 $h^{-1}$; a $H_2$ flow of 100 to 800 nl $H_2$/l feed. The hydroisomerisation reaction may be in the presence of an isomerisation catalyst, such as a catalyst comprising a Group VIII metal and a molecular sieve, optionally on an alumina and/or silica support.

The hydrodeoxygenation and isomerisation catalyst may be the same, such as for example NiW.

The invention in its second aspect relating to the use of the ketonisation catalyst selected as a metal oxide comprising essentially titanium as metal, in particular $TiO_2$, for improving catalyst life time, in particular relates to the following embodiments taken alone or in combination:

The use wherein the fatty acid ketonisation stage may comprise fatty acids selected from $C_{12}$-$C_{43}$-fatty acids.

The use wherein the fatty acid hydrooxygenation stage may comprise ketones selected from $C_{12}$-$C_{43}$-ketones.

The renewable base oil according to the present invention may be highly paraffinic in that it is derived from ketonisation of fatty acids. Accordingly, the renewable base oil may comprise very little aromatics or oxygenates. Being a base oil, it boils within a base oil boiling range, such as above 380° C.

A renewable diesel fuel is a hydrocarbon diesel product as opposed to e.g. oxygen-containing biodiesel, which are mono-alkyl fatty acid esters of biological oils. Being a diesel fuel, it boils within a diesel boiling range, such as between 180 and 380° C., for example between 180° C. or 210° C. and 350° C., for example diesel fuel according to EN15940 or for example a diesel fuel component for a diesel fuel according to EN 590.

Common to the renewable base oil, diesel or naphtha are that they may be highly paraffinic, in that the content of aromatics and/or oxygenates is very low, such as below 0.5 vol %.

The renewable content may be determined from the starting materials, as well as being determined in the products by isotopic distribution involving $^{14}C$, $^{13}C$ and/or $^{12}C$ as described in ASTM D6866.

The feedstock comprises as the major part a mixture of free fatty acids and fatty acid esters, such as fatty acid glycerols. This is because the ketonisation reaction requires free fatty acids and because degraded or low-value biological oils are typically mixtures of free fatty acids and fatty acid glycerols, such as triglycerides or partial glycerides. The major part of the free fatty acids and fatty acid esters may be considered to be more than 50 wt %, such as more than 70 wt %, more than 90 wt %.

In degraded biological oil, part of the triglycerides, which can be used as high-value edible oils have been degraded to free fatty acids and partial glycerides, such as mono- and di-glycerides. The low-value biological oils may therefore have a higher amount of free fatty acids compared to the glyceride content (combined amount of mono-, di- and tri-glycerides). For example, in the refining of crude palm oil, a palm oil stripper may be used to separate crude palm oil into high-value edible palm oil and low-value palm oil fatty acid distillate (PFAD). The low-value PFAD is not fit for human consumption, and may advantageously be used in the methods according to the present invention.

Accordingly, the feedstock in one embodiment of the invention may be palm oil fatty acid distillate (PFAD), which contains as the major part free fatty acids. PFAD is one example of low-value biological oils containing free fatty acids and fatty acid esters such as partial glycerides. Such degraded fats are unsuited for food production and need to be removed during the palm oil refining process before the palm oil meets the food industry's quality standards. The fatty acid composition of PFAD varies by source. It is typically desirable to keep the degraded free fatty acid content low in edible oils, such as palm oil, which is for the most part comprises of triglycerides. PFAD is a by-product that is unsuited for food production. It has a higher content of free fatty acids than triglycerides (because the palm oil triglycerides are used as the edible palm oil), such as a higher amount of free fatty acids compared to the fatty acid ester content.

Palm oil fatty acid distillate (PFAD) is a by-product from refining crude palm oil. It is a light brown semi-solid at room temperature, which melts to a brown liquid on heating. While the composition of PFAD varies, the minimum free fatty acid (FFA) content of PFAD may be 60 wt %. The contractual specifications the providers of PFAD are asked to fulfil often specifies 70 wt % or more FFA, which means that the FFA content is often 80 wt % or more. The FFA content may be in the range of 65-95 wt %, such as between 80-90 wt %.

The PFAD also contains fatty acid glycerols selected from mono-glycerides, di-glycerides and tri-glycerides of fatty acids. For example the fatty acid glycerol content may be above 2 wt % or below 20 wt %, for example in the range of 2-15 wt %.

The remaining components of PFAD may be unsaponifiable matters, such as tocopherol, tocotrienols, sterols, squalenes and volatile substances. For example, the unsaponifiable matter content may be above 0.5 wt % or below 3 wt %, for example in the range of 0.5-2.5 wt %.

PFAD may additionally comprise trace metals, for example Cr, Ni, Cu, Fe.

Bonnie Tay Yen Ping and Mohtar Yusof published in 2009 Characteristics and Properties of Fatty Acid Distillates from Palm Oil in Oil Palm Bulletin 59, p. 5-11, which provide updated information on the composition of PFAD, which is incorporated herein by reference.

While one example of a feedstock of biological origin according to the present invention is PFAD, there are many other well-suited feedstocks of biological origin, such as other plant oils or animal fat that have contain free fatty acids, various grades of and products from the refining of plant oil or animal fat, waste cooking oil, various grades of and products from tall oil refining, crude tall oil (CTO), tall oil, tall oil fatty acids (TOFA), yellow grease, poultry fat, fish oil or acid oil side products of for example oleochemicals production.

The feedstock of biological origin may further be mixtures of a number of different feedstocks of biological origin. For example one or more kinds of plant oils or animal fats having more free fatty acids than fatty acid esters mixed with one or more kinds of plant oils or animal fats having less free fatty acids than fatty acid esters.

While the feedstock comprises as the major part a mixture of free fatty acids and fatty acid esters, such as fatty acid glycerols, the amounts of FFA and of fatty acid esters may vary considerably, as evident from the many different types the free fatty acid content and fatty acid ester feedstocks and mixtures mentioned above.

For practical purposes the feedstock may comprise at least 2 wt % free fatty acids, such as at least 5 wt %. For example, some separation methods, such as distillation, are more efficient when the mixture of free fatty acids is at least 5 wt %, such as at least 7 wt % or 10 wt %. The fatty acid content may be below 98 wt %, such as below 95 wt %, or below 90 wt %

For practical purposes the feedstock may comprise at least 2 wt % fatty acid esters, such as at least 5 wt %. For example, some separation methods, such as distillation, are more efficient when the content of fatty acid esters is at least 5 wt %, such as at least 7 wt % or at least 10 wt %. The fatty acid ester content may be below 98 wt %, such as below 95 wt %, or below 90 wt %

For example the mixture of free fatty acids may be 2-95 wt %, for example 5-95 wt %, such as 5-90 wt % of a mixture of free fatty acids. In some feedstocks, the free fatty acid content is rather high, such as above 50 wt % or above 70 wt %.

For example the mixture of fatty acid glycerols selected from mono-glycerides, di-glycerides and tri-glycerides of fatty acids may be 5-98 wt %, for example 5-95 wt %, such as 5-90 wt % of a mixture of free fatty acids. In some feedstocks, the free fatty acid content is rather high, such as above 50 wt % or above 70 wt %.

The feedstock may for example comprise 5-90 wt % free fatty acids, 5-90 wt % fatty acid glycerols, and less than 0-20 wt % of one or more compounds selected from the list consisting of: fatty acid esters of the non-glycerol type, fatty amides, and fatty alcohols, where the feedstock comprises more than 50 wt % of free fatty acids and fatty acid glycerols, such as 70 wt % or more, for example 80 wt % or more.

It is possible to increase the fatty acid content of the feedstock thereby potentially providing more renewable base oil in the process by prior to step a) of the method, an initial feedstock comprising fatty acid esters may be pretreated in at least a hydrolysis step, such as partial hydrolysis, thereby producing the feedstock, where the ratio of free fatty acids to fatty acid esters has been increased compared to the initial feedstock.

The fatty acids may be saturated and unsaturated. When desiring to manufacture dimer products in the ketonisation reaction, it is advantageous that the fatty acids are saturated fatty acids or have a reduced amount of unsaturation because double bond oligomerisations, which may lead to tarry products are then avoided or reduced. For example, the major part of the free fatty acid feed may be saturated free fatty acids. Advantageously, more than 90 wt % of the free fatty acid feed is saturated fatty acids, such as more than 95 wt % or more than 99 wt %.

The saturated fatty acids may be obtained from a double-bond hydrogenation reaction of either the feedstock prior to separating it into a free fatty acid feed and one or more free fatty acid depleted feed(s) or double bond hydrogenation of the free fatty acid feed after separation. For example a prehydrogenation step may utilise a hydrogenating catalyst, for example as described below under the heading "Hydrodeoxygenation of the ketone stream"—for example NiMo on an alumina support, but preferably double bond hydrogenation is done with supported a noble metal, such as Pd or Pt on Silica or carbon support, which tends to be efficient in double bond hydrogenation. The prehydrogenation may be conducted at a temperature below 300° C., such as below 280° C. or below 260° C. in order to avoid hydrodeoxygenation reactions. The prehydrogenation may also be above 90° C., such as above 110° C. or above 120° C. in order to be high enough to ensure sufficient hydrogenation of the double bonds. For example the temperature for prehydrogenation may be 90-300° C., such as 110-280° C., for example 120-260° C. The pressure may be 10-70 barg, such as 20-60 barg, for example 30-50 barg. The WHSV may be 0.5-3.0 $h^{-1}$, such as 1.0-2.5 $h^{-1}$, for example 1.0-2.0 $h^{-1}$. The $H_2$/oil ratio may be 100-500 nl/l, such as 150-450 nl/l, for example 200-400 nl/l. Accordingly, the prehydrogenation may preferably be conducted at 90-300° C., 10-70 barg, WHSV of 0.5-3.0 $h^{-1}$, and $H_2$/oil ratio of 100-500 nl/l; more preferably at 110-280° C., 20-60 barg, WHSV of 1.0-2.5 $h^{-1}$, and $H_2$/oil ratio of 150-450 nl/l; even more preferably at 120-260° C., 30-50 barg, WHSV of 1.0-2.0 $h^{-1}$, and $H_2$/oil ratio of 200-400 nl/l.

The saturated fatty acids may also be present in the feedstock itself, and separation may further improve the part of free fatty acids that are saturated. For example PFAD typically contains around 30-40 wt % $C_{16}$ saturated fatty acids together with around 50 wt % $C_{18}$ saturated and unsaturated fatty acids, and less than 5 wt % fatty acids below $C_{14}$. This makes PFAD or PFAD containing mixtures advantageous feedstocks because the large amount of $C_{16}$ saturated fatty acids can be separated from the remaining feedstock, thereby obtaining a free fatty acid feed having a higher amount of free fatty acids, in particular having a higher amount of saturated free fatty acids, which are advantageous when wanting to manufacture dimer products in the ketonisation reaction.

Separation of the Feedstock

The method may involve a step of separating the feedstock into at least: a free fatty acid enriched which feed is having a higher concentration of free fatty acids than the feedstock, and one or more free fatty acid depleted feed(s) which feed(s) is having a higher concentration of the compounds selected from mono-glycerides, di-glycerides, tri-glycerides of fatty acids than the feedstock and having a higher boiling point than the free fatty acid enriched feed.

The free fatty acid enriched feed may e.g. have a concentration of free fatty acids that is at least 5% higher, such as at least 10% higher, at least 15% higher, at least 20% higher or at least 25% higher, than the free fatty acid concentration in the feedstock. The free fatty acid enriched feed may e.g. have a concentration of fatty acid glycerols selected from mono-glycerides, di-glycerides and tri-glycerides of fatty acids below 5 wt %.

The free fatty acid depleted feed(s) may e.g. have a concentration of the compounds selected from mono-glycerides, di-glycerides, tri-glycerides of fatty acids that is at least 5% higher, such as at least 10% higher, at least 15% higher, at least 20% higher or at least 25% higher, than said concentration in the feedstock. The free fatty acid depleted feed(s) may e.g. have a concentration of free fatty acids below 2 wt %.

The separation step may for example be distillation, but other methods, such as crystallisation by cooling, or a combination of distillation and crystallisation may be used.

The separation may for example be distillation, such as at a temperature between 100° C. to 300° C., and at a distillation pressure of 0.5 kPa to 5 kPa.

The feedstock or the free fatty acid enriched feed may be $C_{10}$-$C_{24}$ fatty acids, preferably $C_{14}$-$C_{22}$, such as one or more of $C_{14}$, $C_{16}$, $C_{18}$, $C_{20}$ and $C_{22}$ fatty acids The one or more free fatty acid depleted feed(s) has a higher concentration of the compounds selected from mono-glycerides, di-glycerides and tri-glycerides of fatty acids.

The one or more free fatty acid depleted feed(s) may have a higher boiling point than the free fatty acid feed and/or have a higher average molecular weight. For example the higher boiling point can be a higher final boiling point compared to the free fatty acid feed and the higher average molecular weight can be measured as a weighted average. The boiling points may for example be measured using SimDist GC boiling point plots according to ASTM D 2887.

The feedstock usually contains both $C_{16}$ and $C_{18}$ fatty acids, which may be separated by distillation for example, and the major part of the free fatty acid feed may be $C_{16}$ fatty acids.

Ketonisation

The feedstock or the free fatty acid enriched feed that has been separated from the feedstock is subjected to ketonisation reaction conditions where two fatty acids react to yield a ketone stream, the ketone stream comprising as the major part ketones.

The ketonisation reaction yields both water and carbon dioxide, which may be separated from the oil fraction, for example water may be separated by decanting, and carbon dioxide and other gaseous components may be separated in a flash drum.

The ketonisation reaction conditions may comprise one or more of the following: a temperature in the range from 300 to 400° C.; a pressure in the range from 5 to 30 barg; a WHSV in the range from 0.25 to 3 $h^{-1}$.

For example the ketonisation reaction conditions may involve a temperature in the range from 300 to 400° C.; a pressure in the range from 5 to 30 barg; a WHSV in the range from 0.25 to 3 $h^{-1}$. Preferably the ketonisation reaction conditions may involve a temperature in the range from 330 to 370° C.; a pressure in the range from 10 to 25 barg; a WHSV in the range from 0.5 to 2 $h^{-1}$. More preferably the ketonisation reaction conditions may involve a temperature in the range from 340 to 360° C.; a pressure in the range from 15 to 20 barg; a WHSV in the range from 1.0 to 1.5 $h^{-1}$.

The ketonisation reaction is conducted in the presence of a ketonisation catalyst, the ketonisation catalyst is selected as a metal oxide catalyst comprising essentially titanium as the metal.

For example, the ketonisation catalyst may be $TiO_2$, optionally on a support, such as for example $TiO_2$ in anatase form having an average pore diameter of 80-160 Å, and/or a BET area of 20-140 $m^2$/g, and/or porosity of 0.1-0.3 $cm^3$/g.

The ketonisation reaction may be pressurised by a gas. For example the ketonisation may be conducted in the presence of a gas in the range from 0.1-1.5 gas/feed ratio (w/w), the gas being selected from one or more of: $CO_2$, $H_2$, $N_2$, $CH_4$, $H_2O$. The gas used for pressurisation may advantageously be $CO_2$ as it is produced as a by-product of the ketonisation reaction and can be recycled as a pressurisation gas.

The ketonisation reaction conditions may be selected such as to ensure liquid phase ketonisation, or at least that the feed introduction to the ketonisation step is in liquid form. By ensuring liquid phase ketonisation, by suitable selection of a combination of catalyst, pressure and temperature, the reaction results in less undesired by-products, compared to gas phase ketonisation.

The ketonisation reaction conditions may include $TiO_2$ as the ketonisation catalyst, and may ensure that the content of metal impurities in the feedstock or the free fatty acid enriched feed immediately before it is subjected to the ketonisation reaction conditions and in the ketone stream obtained immediately after it has been subjected to the ketonisation reaction conditions comprise at most 20 ppm manganese, at most 20 ppm magnesium, at most 20 ppm calcium, at most 20 ppm potassium, measured using inductively coupled plasma (ICP) metal analysis. In this context it is the content of metal impurities in the oil phase of the ketone stream obtained immediately after ketonisation that is ensured to be on the specified levels.

Such ketonisation reaction conditions may further ensure that the ketone stream obtained immediately after it has been subjected to the ketonisation reaction conditions comprises at most 5 ppm manganese, at most 5 ppm magnesium, at most 5 ppm calcium, at most 5 ppm potassium, measured using inductively coupled plasma (ICP) metal analysis.

For example, such ketonisation reaction conditions may ensure that the ketone stream obtained immediately after it has been subjected to the ketonisation reaction conditions comprises at most 3 ppm manganese, at most 3 ppm magnesium, at most 3 ppm calcium, at most 3 ppm potassium, measured using inductively coupled plasma (ICP) metal analysis.

The ketone stream comprises dimers of the free fatty acid feed. For example, if the feedstock or the free fatty acid enriched feed is exclusively palmitic acid (C16:0 fatty acid), then the ketone stream will produce a $C_{31}$ ketone, and if the free fatty acid feed is a mixture of $C_{16}$ and $C_{18}$ fatty acids, then the ketone stream will produce a mixture of $C_{31}$, $C_{33}$, and $C_{35}$ ketones.

As mentioned above, the free fatty acid stream may be a saturated free fatty acid feed. This reduces the amount of unwanted oligomerisation product. If the free fatty acid feed contains unsaturated free fatty acids, these free fatty acids may be saturated by hydrogenation. Such a prehydrogenation step is usually conducted under mild conditions in the presence of a hydrogenation catalyst at temperatures between 50 and 400° C., under a hydrogen pressure ranging from 0.1 to 20 MPa, preferably at temperatures between 150 and 300° C., under a hydrogen pressure ranging from 1 to 10 MPa. The prehydrogenation catalyst contains metals of the Group VIII and/or VIA of the periodic system of the elements. The prehydrogenation catalyst is preferably a supported Pd, Pt, Rh, Ru, Ni, Cu, CuCr, NiMo or CoMo catalyst, the support being activated carbon, alumina and/or silica.

However, it is desirable that no hydrogenation of free fatty acids is carried out. In particular the palmitic acid (saturated free fatty acid) in PFAD may be separated by distillation, thus yielding a saturated free fatty acid feed of palmitic acid without any hydrogenation necessary.

Accordingly, in certain variants of the present invention, no pre-treatment by hydrogenation or by hydrolysis is done in step a) or in-between other steps of the method.

The ketonisation reaction of the free fatty acid feed may be run under conditions that result in almost complete (>90%, >95%, >99% or even ≥99.5%) conversion of the free fatty acids into ketones, as there is less undesired oligomerisation reaction compared to ketonisation of the entire stream. This provides distinct advantages downstream, in that hydrodeoxygenation of the ketone stream requires less severe hydrodeoxygenation conditions in order to ensure complete deoxygenation of the ketone feed, compared to e.g. the free fatty acid depleted feed, which may contain both free fatty acids and fatty acid glycerols. Less severe conditions, for example lower reaction temperature in the hydrodeoxygenation step results in less energy used a reduction in undesirable side reactions, such as coking, leading to a longer catalyst life time.

Sometimes, formation of heavies (fatty acid trimers) during the above-mentioned almost complete conversion (>99.5 wt-%) is observed. The fatty acid trimers may increase the viscosity of the base oil end-product. This should preferably be avoided, because low viscosity is desirable in order to low fuel consumption. The present inventors have observed that it is possible with the metal oxide catalyst used according to the invention, in particular the $TiO_2$ catalyst, to obtain an almost conversion (>99.5 wt-%) with high selectivity in comparison with the prior art catalyst, e.g. $K_2O/TiO_2$, and at the same time keep the formation of heavies at 2.5% or lower.

Thus, there are at least three observed advantages related to the metal oxide catalyst comprising essentially titanium as metal, in particular the $Ti_2O$ catalyst: First, the ketonisation step shows highly selective conversion (99.5% or more) of the fatty acids into ketones and at the same time formation of 2.5% fatty acid trimers or less, whereby the subsequent hydrodeoxygenation can be conducted at milder reaction conditions. Second, substantially no metal leaching is observed during the start-up of the fatty acid ketonisation; metal leaching from the ketonisation catalyst, in particular in the first 3-4 weeks, is important for and will influence negatively the life time of the subsequent hydrodeoxygenation catalyst. Metal leaching will increase the fouling of the reactor and increase the pressure drop of the catalyst bed (plugging of the catalyst bed) and also deactivate the hydrodeoxygenation catalyst, thus the life time of this catalyst is significantly improved. For example every ppms of impurity in feed of commercial production unit means over 21 kg metals/month, over 250 kg/year (30 tons feed rate), which stays on the top of the catalyst bed and eventually plug the reactor. And third, the $Ti_2O$ catalyst is not decomposed during the ketonisation step, thus the catalyst life time is improved.

Hydrodeoxygenation and Isomerisation of the Ketone Stream

The ketone stream obtained from the ketonisation reaction may be isolated by decanting the water from the oil and separating the gaseous products from the liquid products, for example in a flash drum. The ketone stream is then subjected to both hydrodeoxygenation reaction conditions and to hydroisomerisation reaction conditions.

The hydrodeoxygenation and hydroisomerisation reaction conditions may either be done simultaneously or in sequence. The product is a deoxygenated and isomerised base oil stream comprising the renewable base oil.

The hydrodeoxygenation reaction may be performed in the presence of a hydrodeoxygenation catalyst, such as CoMo, NiMo, NiW, CoNiMo on an support, for example an alumina support. The hydrodeoxygenation catalyst may be typical hydrodeoxygenation catalysts in the art, for example it may comprise a hydrogenation metal on a support, such as for example a catalyst selected from a group consisting of Pd, Pt, Ni, Co, Mo, Ru, Rh, W or any combination of these. The hydrodeoxygenation step is done under hydrodeoxygenation conditions to provide the base oil product. The hydrodeoxygenation step may for example be conducted at a temperature in the range from 250 to 400° C. and at a pressure in the range from 20 to 80 barg, a WHSV in the range from 0.5 to 3 $h^{-1}$, and a $H_2$/oil ratio of 350-900 nl/l, using a catalyst, such as NiMo, optionally on a alumina support.

Preferably, the hydrodeoxygenation condition may involve a temperature in the range from 280 to 350° C.; a pressure in the range from 30 to 60 barg; a WHSV in the range from 1.0-2.5 $h^{-1}$; and a $H_2$ flow of 350-750 nl $H_2$/l feed. The catalyst may be NiMo on alumina support.

In particular, the hydrodeoxygenation condition may involve a temperature in the range from 300 to 330° C.; a pressure in the range from 40 to 50 barg; a WHSV in the range from 1.0 to 2.0 $h^{-1}$; and a $H_2$ flow of 350 to 500 nl $H_2$/l feed. The catalyst may be NiMo on alumina support.

Further in the process, the ketone stream may be diluted with a stream of hydrocarbons. The dilution may be 30 wt % hydrocarbons and 70 wt % ketone stream, for example between 30-85 wt % hydrocarbon and 15-70 wt % ketone stream. The stream of hydrocarbons used for dilution may in part of fully be product recycle.

The product recycle may have undergone fractionation before being recycled, for example it may be the fraction boiling above 380° C. that is recycled, or any other fraction of the base oil mixture described herein.

As mentioned above hydrodeoxygenation catalyst may for example be a molybdenum or wolfram catalyst, typically on a support, such as $Al_2O_3$. The catalyst may or may not be promoted. Typical promoters are Ni and/or Co. Promoted hydrodeoxygenation catalysts may for example be NiMo, CoMo, NiW, CoW, NiCoMo. When a wolfram based catalyst is used, such as a NiW, or a Pd or Pt catalyst it has the further advantage that it can also catalyse isomerisation reactions, thus enabling a simultaneous hydrodeoxygenation and hydrosiomerisation reaction. Accordingly, the hydrodeoxygenation and isomerisation catalyst may be the same, such as for example NiW, or a Pt catalyst, such as Pt/SAPO in mixture with a promoted Mo catalyst on a support, e.g. NiMo on alumina.

The hydrodeoxygenation is done in the presence of hydrogen gas in a hydrodeoxygenation zone, which may be a catalyst bed in a fixed bed reactor.

When the hydrodeoxygenation and hydroisomerisation take place in sequence, in-between the hydrodeoxygenation and hydroisomerisation there may be a stripping step, where gasses are separated from liquids. This may occur in a high temperature and high pressure separation step, for example at a temperature in the range from 300 to 330° C. and at a pressure in the range from 40 to 50 barg.

Hydroisomerisation of the Ketone Stream

The product of the hydrodeoxygenation step is subjected to an isomerization step in the presence of hydrogen and an isomerization catalyst. Both the hydrotreatment step and isomerisation step may be conducted in the same reactor, and even in the same reactor bed. The isomerisation catalyst may be a noble metal bifunctional catalyst such as a Pt containing commercial catalyst, for example Pt-SAPO or Pt-ZSM-catalyst or for example a non-noble catalyst, such as NiW. The hydrodeoxygenation and hydroisomerisation steps may be done in the same catalyst bed using e.g. the NiW catalyst in both the hydrotreatment and isomerisation step. The NiW catalyst may additionally result in more hydrocracking to diesel and naphtha products, and may be an advantageous catalyst if such products are also desired together with the renwable base oil product. The isomerization step may for example be conducted at a temperature of 250-400° C. and at a pressure of 10-60 barg. As explained elsewhere in this description, it is desirable to reduce the severity of the isomerisation reaction to avoid or reduce the amount of cracking of the renewable base oil product. The isomerisation step may for example be conducted at a temperature of 250-400° C., at a pressure of between 10 and 60 barg, a WHSV of 0.5-3 $h^{-1}$, and a $H_2$/oil ratio of 100-800 nl/l.

The hydrodeoxygenation and hydroisomerisation reactions may be done in sequence. The sequence is typically hydrodeoxygenation followed by hydroisomerisation, but this sequence may also be reversed.

The isomerisation reaction conditions may comprise one or more of the following: a temperature in the range from 250 to 400° C.; a pressure in the range from 10 to 60 barg; a WHSV in the range from 0.5 to 3 $h^{-1}$; a $H_2$ flow of 100 to 800 nl $H_2$/l feed.

Preferably the isomerisation reaction conditions comprise a temperature in the range from 280 to 370° C.; a pressure in the range from 20 to 50 barg; a WHSV in the range from 0.5 to 2.0 $h^{-1}$; a $H_2$ flow of 200-650 nl $H_2$/l feed.

More preferably the isomerisation reaction conditions comprise a temperature in the range from 300 to 350° C.; a pressure in the range from 25 to 45 barg; a WHSV in the range from 0.5 to 1.0 $h^{-1}$; a $H_2$ flow of 300-500 nl $H_2$/l feed.

The hydroisomerisation reaction may be in the presence of an isomerisation catalyst, such as a catalyst comprising a Group VIII metal, preferably Pt, and a molecular sieve, optionally on an alumina and/or silica support. The molecular sieve may for example be zeolites, such as ZSM or aluminophosphate molecular sieves, such as SAPO, such as SAPO-11, MeAPO, MeAPSO, where Me is e.g. Fe, Mg, Mn, Co or Zn, or other elements (EI) molecular sieves EIAPO or EIAPSO. For example silica-alumina, Y zeolite, SAPO-11, SAPO-41, ZSM-22, ferrierite, ZSM-23, ZSM-48, ZBM-30, IZM-1, COK-7. Suitable molecular sieves and characteristics of molecular sieves suitable for hydroisomerisation applications are known to the skilled person, and have been described in the literature, such as in Handbook of heterogeneous catalysis from VCH Verlagsgesellschaft mbH with editiors Ertl, Knözinger and Weitkamp, volume 4, pages 2036-2037, which is hereby incorporated by reference herein.

Purifying the Base Oil

In the embodiment of claim 2, between steps c) and d) of the method, there may be a stripping step, where gasses are separated from liquids. This may for example be done at a temperature in the range from 320 to 350° C. and as pressure in the range from 3-6 barg.

In this embodiment, between steps c) and d), and preferably after the stripping step, if present, there may also be an optional hydrofinishing step, where the product are stabilised by conducting a further hydrogenation step in the presence of a hydrogenating catalyst, for example as described above under the heading "Hydrodeoxygenation of the ketone stream"—for example NiMo on an alumina support. However, other hydrofinishing catalysts containing metals of the Group VIII of the periodic system of the elements on e.g. an alumina and/or silica support may also be used. The hydrofinishing catalyst is preferably a supported Pd, Pt, or Ni catalyst, the support being alumina and/or silica.

The hydrofinishing step is similar to the prehydrogenation step with regards to the reaction conditions. However, in the hydrofinishing step, typically higher pressures, and to some extent higher temperatures are utilised. This is because the feed is fully deoxygenated at this stage compared to a potential prehydrogenation step. The hydrofinishing step is present in order to stabilise the product, which among other things involves hydrogenation of double bonds or aromatic compounds that is present or has formed during the previous steps, such as during hydroisomerisation. The hydrofinishing step may be conducted at a temperature below 300° C., such as below 280° C. or below 260° C. The hydrofinishing may also be above 180° C., such as above 190° C. or above 200° C. For example the temperature for prehydrogenation may be 180-300° C., such as 190-280° C., for example 200-250° C. The pressure may be 100-200 barg, such as 120-180 barg, for example 140-160 barg. The WHSV may be 0.5-3.0 h$^{-1}$, such as 0.75-2.5 h$^{-1}$, for example 1.0-2.0 h$^{-1}$. The H$_2$/oil ratio may be 100-500 nl/l, such as 150-450 nl/l, for example 200-400 nl/l. Accordingly, the prehydrogenation may preferably be conducted at 90-300° C., 10-70 barg, WHSV of 0.5-3.0 h$^{-1}$, and H$_2$/oil ratio of 100-500 nl/l; more preferably at 110-280° C., 20-60 barg, WHSV of 1.0-2.5 h$^{-1}$, and H$_2$/oil ratio of 150-450 nl/l; even more preferably at 120-260° C., 30-50 barg, WHSV of 1.0-2.0 h$^{-1}$, and H$_2$/oil ratio of 200-400 nl/l.

For example the deoxygenated and isomerised base oil stream may be distilled to obtain the renewable base oil in a fraction having a boiling point of more than 380° C., such as more than 410° C., for example more 450° C. or more, such as 470° C. or more, such as 480° C. or more, or for example 500° C. or more.

During distillation other fractions, such as a naphtha fraction and/or a diesel fraction may also be isolated. These fractions are the result of cracking during the hydrodeoxygenation and hydroisomerisation reactions, as well as a very little amount of unconverted free fatty acid from the ketonisation step.

Hydrodeoxygenation and Isomerisation of the FFA Depleted Feed(s)

The one or more free fatty acid depleted feed(s) may be transformed into a middle distillate product, such as a diesel product, preferably in be subjected to both hydrodeoxygenation reaction conditions and to hydroisomerisation reaction conditions, simultaneously or in sequence, to yield a deoxygenated and isomerised diesel stream comprising the diesel fuel; optionally distilling the stream obtained to obtain a distilled diesel fuel.

This may be done in the same manner as described under the heading "Hydrodeoxygenation and isomerisation of the ketone stream". The one or more free fatty acid depleted feed(s) may also be diluted with a stream of hydrocarbons before the hydrodeoxygenation and hydroisomerisation. The dilution may be 30 wt % hydrocarbons and 70 wt % stream, for example between 30-85 wt % hydrocarbon (diluent) and 15-70 wt % free fatty acid depleted feed (fresh feed). The dilution may also be high for example 3:1 and up to 20:1, for example 4:1 and up to 20:1, such as 5:1 and up to 20:1 (hydrocarbons:fresh feed) The stream of hydrocarbons used for dilution may in part or fully be product recycle.

The product recycle may have undergone fractionation before being recycled, for example it may be the fraction boiling in the diesel range of around 180-350° C., such as 210-350° C., that is recycled.

Renewable Base Oil, Diesel and Naphtha

The method according to the present invention produces renewable base oil and a renewable diesel. In the course of production, the renewable base oil will also comprise small amounts of renewable diesel and naphtha as explained above. The deoxygenated and isomerised diesel streams comprise in addition to the renewable diesel fuel small amounts of renewable naphtha, which can be separated and pooled with the renewable naphtha from the renewable base oil fractionation, and the renewable diesel obtained from distillation of the deoxygenated and isomerised diesel stream can be pooled with the renewable diesel from the renewable base oil fractionation.

Accordingly, the process may additionally be for producing a naphtha fuel, where the naphtha fuel is obtained from distillation of both the deoxygenated and isomerised base oil stream and from the distillation of the deoxygenated and isomerised diesel stream.

For example the combined amounts of renewable naphtha, diesel and base oil obtained from the feedstock of biological origin may be between 5-95 wt % renewable base oil, 5-95 wt % diesel, and 0-30 wt % naphtha; for example between 5-95 wt % renewable base oil, 5-95 wt % diesel, and 5-30 wt % naphtha.

THE INVENTION WILL NOW BE DESCRIBED WITH REFERENCE TO THE FIGURES

FIG. 1 describes a method for producing a renewable base oil from a feedstock of biological origin denoted "PFAD". While the feedstock of biological origin in FIG. 1 has been denoted PFAD, the method in FIG. 1 is not limited to PFAD, but may be any feedstock of biological origin as described herein.

The method comprises a step a) of providing the feedstock of biological origin as described herein, in particular under the heading "Feedstock" above. The feedstock of biological origin denoted "PFAD" is then separated into at least a free fatty acid feed by distillation denoted "FFA distillation", where a distillate having a higher concentration of free fatty acids than the feedstock is obtained. Reference is made to the section above titled "Separation of the feedstock". The free fatty acid feed obtained from the "FFA distillation" is then subjected to ketonisation reaction conditions (denoted "Ketonisation") where two fatty acids react to yield a ketone stream, the ketone stream comprising as the major part ketones. Reference is made to the section above titled "Ketonisation" for additional details about the ketonisation step.

The ketone stream is then subjected to hydrodeoxygenation reaction conditions, denoted "HDO", where hydrogen is also supplied. When the hydrodeoxygenation and hydroisomerisation steps take place in sequence rather than simultaneously, the deoxygenated base oil stream may be stripped of water and gasses in a stripping step, denoted "intermediate stripper". The HDO step may be as described above under the heading "Hydrodeoxygenation of the ketone stream", and the stripping step may be as described above under the heading "Purifying the base oil". The deoxygenated base oil may then be subjected to hydroisomerisation reaction conditions, denoted "Isomerisation", where hydrogen is also supplied, yielding a deoxygenated and isomerised base oil stream comprising the renewable base oil. The hydroisomerisation conditions may be as described above under the heading "Hydroisomerisation of the ketone stream". When the hydrodeoxygenation and hydroisomerisation step takes place simultaneously, as for example as described under the heading "Hydroisomerisation of the ketone stream", then the "HDO" and "Isomerisation" are one and same reactor, and the "intermediate stripper" is placed downstream of the simultaneous hydrodeoxygenation and hydroisomerisation. The deoxygenated and isomerised base oil stream may optionally be stabilised denoted "Product stabilization", for example as disclosed above under the heading "Purifying the base oil".

The method also comprises a step of distilling the product to obtain a distilled renewable base oil, typically under vacuum, denoted "Vacuum distillation", for example as disclosed above under the heading "Purifying the base oil". The distillation may yield one or more fractions of renewable base oils, collectively denoted "RBO", for example above 380° C., for example a fraction between 380-450° C. and an fraction above 450° C.

By-products from the product stabilization and fractions other than the RBO fractions from the vacuum distillation may be directed as streams to fuel production denoted "Stream to fuel production", for example for the production of one or more fractions in the naphtha boiling range, such as below 180° C. and diesel boiling range, 180-350° C., for example as described above under the heading "Renewable base oil, diesel and naphtha".

FIG. 2, describes in addition to the "PFAD", "FFA distillation", "Ketonisation", "HDO", "intermediate stripper", "Isomerisation", "Product stabilization", "Vacuum distillation", and "RBO" of FIG. 1, three elements, which can be used together with the method either alone or in combination.

The first element is shared support units for base oil and diesel production ("Shared support units for baseoil and diesel production"), which may involve the removal of water formed during the ketonisation reaction and the hydrodeoxygenation by stripping or decantation (for example in the form of a sour water stripper denoted "Sour water stripper" in FIG. 3). The shared support units additionally provides for the possibility of having a recycle gas loop in order to recycle hydrogen from the hydrodeoxygenation step ("HDO") or from the diesel fuel production ("Diesel fuel production"), optionally purifying the hydrogen gas by removal of e.g. steam in a stripper before being fed to the ketonisation step ("Ketonization") as a pressurising gas for the ketonisation reaction, as for example disclosed above under the heading "Ketonisation".

The second element is the hydrofinishing step for saturation of potential aromatic compounds or double bonds present in order to stabilise the product ("Product stabilisation"), as described above under the heading "Purifying the base oil". The product stabilization will also stabilise the potential naphtha boiling range ("Naphta stabilization") and diesel boiling range ("Diesel stabilization") compounds present in the renewable base oil due to e.g. cracking during hydroisomerisation and/or from the FFA that did not react in the ketonisation reaction and was carried forward. The vacuum distillation ("Vacuum distillation") of the renewable base oil may therefore yield one or more fractions of renewable base oils, collectively denoted "RBO", for example above 380° C., for example a fraction between 380-450° C. and an fraction above 450° C., as well as one or more fractions in the Naphtha boiling range, such as below 180° C. and diesel boiling range, 180-350° C., for example as described above under the heading "Renewable base oil, diesel and naphtha".

The third element is the separation step ("FFA distillation"). The separation of the feedstock of biological origin ("PFAD") into a free fatty acid feed, which is processed into renewable base oil ("RBO") via ketonisation, and a bottom stream ("Bottom stream"), which can for example be further processed into a diesel fuel ("Diesel fuel production"). The separation step ("FFA distillation") allows for a more versatile production of renewable base oil ("RBO"), both in respect of quality of the RBO, as well as the quantity. With regards to the quality, the FFA distillation can, as shown in example 1, produce a free fatty acid feed essentially consisting only of e.g. palmitic acid. This single carbon fatty acid can then be processed via ketonisation to renewable base oil which consists essentially of $C_{31}$ base oil having a well-defined composition, which is an industrially relevant product for base oil producers in that they are able to fine tune the particular properties required of base oils.

With regards to the quantity, the separation step also provides for an RBO production that can be scaled depending on the demand of the market for either renewable base oil or renewable diesel; if more diesel is demanded than base oil, the separation step can for example take a more narrow cut of exclusively palmitic acid and produce a base oil with a very well-defined composition, whereas if less renewable diesel is demanded by the market, the separation step can for example take a more broad cut of the feedstock of biological origin, which may for example include both the $C_{16}$ and $C_{18}$ fatty acids, which can be processed into renewable base oil products via ketonisation, yielding RBO mixtures comprising $C_{31}$, $C_{33}$ and $C_{35}$ base oils. The amount of free fatty acids in a feedstock of biological origin as defined herein (see e.g. the section titled "feedstock") may be further increased by prior to step a) of the method, the initial feedstock comprising fatty acid esters may be pre-treated in at least a hydrolysis step thereby producing the feedstock, where the ratio of free fatty acids to fatty acid esters has been increased compared to the initial feedstock.

FIG. 3, describes in addition to FIGS. 1 and 2 that the bottom stream of FIG. 2 is now a fatty acid depleted feed ("renewable diesel line") for the production of diesel in a step f) of subjecting the one or more free fatty acid depleted feed(s) ("renewable diesel line") to an optional prehydrogenation stage ("pretreatment") conducted under mild conditions in the presence of a hydrogenation catalyst, as described under the heading "Ketonisation". The prehydrogenation is intended to saturate double bonds in the remaining fatty acids and fatty acid esters, which enables the use of more severe hydrodeoxygenation conditions in the subsequent step ("HDO").

The HDO step may be as described above under the heading "Hydrodeoxygenation and isomerisation of the FFA depleted feed(s)". The water is separated ("Sour water stripper") in a stripper, which may be shared with the RBO line. Additionally, hydrogen may be recycled via the recycle gas loop, which may also be shared with the RBO line. The deoxygenated diesel stream may then be subjected to hydroisomerisation reaction conditions, denoted "Isomerisation", where hydrogen is also supplied, yielding a deoxygenated and isomerised diesel stream comprising the diesel fuel.

As mentioned above under the section "Hydrodeoxygenation and isomerisation of the FFA depleted feed(s)", the hydrodeoxygenation and hydroisomerisation may be conducted simultaneously or in sequence. The deoxygenated and isomerised diesel stream may optionally be stabilised denoted "Diesel stabilization" and "Naphta stabilization", for example in the form of the hydrofinishing step as disclosed above under the heading "Purifying the base oil". The vacuum distillation ("Vacuum distillation") of the a deoxygenated and isomerised diesel stream may therefore yield one or more fractions of Diesel fuel, collectively denoted "Diesel", in e.g. the boiling range, 180-350° C., as well as one or more fractions in the Naphtha boiling range, such as below 180° C., for example as described above under the heading "Renewable base oil, diesel and naphtha".

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

The terms "comprising", "comprise" and comprises herein are intended by the inventors to be optionally substitutable with the terms "consisting of", "consist of" and "consists of", respectively, in every instance.

EXAMPLES

Example 1—Separation of PFAD into a Palmitic Acid Feed and a Palmitic Acid Depleted Feed Palm fatty acid distillate (PFAD) was separated into a palmitic acid feed and a palmitic acid depleted feed by distillation at a temperature of about 250-275° C. and at 0.01-0.05 bar pressure.

This resulted in a palmitic acid feed, which was 97.0 wt % pure with minor impurities of: $C_{18}$ fatty acids (0.42 wt %); $C_{14}$ fatty acids (2.5 wt %).

The remaining palmitic acid depleted feed contained partial glycerides and $C_{18}$ fatty acids as the primary components:

TABLE 1

| Distillation of PFAD | | | |
|---|---|---|---|
| Carbon number | PFAD feed (wt %) | Distillate (wt %) (Enriched feed) | Bottom (wt %) (depleted feed) |
| C14:0 FFA | 1.1 | 2.5 | 0.0 |
| C16:0 FFA | 42.4 | 97 | 0.4 |
| C18:2 FFA | 1.2 | 0.2 | 2.0 |
| C18:1 FFA | 42.1 | 0.2 | 74.4 |
| C18:0 FFA | 4.5 | 0.01 | 8.0 |
| MG | 0 | 0 | 0.0 |
| DG | 2.6 | 0 | 4.6 |
| TG | 6.1 | 0 | 10.8 |

FFA: free fatty acids;
MG, DG, TG: mono-, di-, tri-glyderides

Example 2—Ketonisation of the Palmitic Acid Feed

The palmitic acid feed was fed to a fixed bed (pilot) reactor operated in continuous mode comprising a catalyst bed loaded with 250 g catalyst material ($TiO_2$ BET 50-54 m²/g; average pore size 100-200 Å; crystallinity 50-100%). The ketonisation was conducted in the liquid phase at a pressure of about 18 bar, temperature of about 360° C., WHSV of about 1.0 h⁻¹, and an extra gas flow of 131 l/h nitrogen. The ketonisation reaction conditions resulted in 85% fatty acid conversion thereby obtaining a ketone stream.

Example 2a—Ketonisation of the Palmitic Acid Feed

The palmitic acid feed was fed to a fixed bed reactor operated in continuous mode comprising a catalyst bed loaded with 20 g catalyst material ($TiO_2$ BET 50-54 m²/g; average pore size 100-200 Å; crystallinity 50-100%). The ketonisation was conducted in the liquid phase at a pressure of about 25 barg, temperature of about 360° C., WHSV of about 0.5 h⁻¹, without extra gas flow. The ketonisation reaction conditions resulted in 99.9% fatty acid conversion thereby obtaining a ketone stream.

Example 2b—Ketonisation of the palmitic acid feed

The palmitic acid feed was fed to a fixed bed (micro) reactor operated in continuous mode comprising a catalyst bed loaded with 20 g catalyst material ($TiO_2$ BET 50-54 m²/g; average pore size 100-200 Å; crystallinity 50-100%). The ketonisatisation was conducted in the liquid phase at a pressure of about 10 barg, temperature of about 360° C., WHSV of about 1.0 h⁻¹, and an extra gas flow of 5 l/h hydrogen. The ketonisation reaction conditions resulted in 99.9% fatty acid conversion thereby obtaining a ketone stream.

Example 2c—Ketonisation of the Palmitic Acid Feed

The palmitic acid feed was fed to a fixed bed reactor operated in continuous mode comprising a catalyst bed loaded with 20 g catalyst material ($TiO_2$ BET 50-54 m²/g; average pore size 100-200 Å; crystallinity 50-100%). The ketonisation was conducted in the liquid phase at a pressure of about 10 barg, temperature of about 360° C., WHSV of about 1.0 h⁻¹, and an extra gas flow of 5 l/h carbon dioxide. The ketonisation reaction conditions resulted in 99.4% fatty acid conversion thereby obtaining a ketone stream.

Example 3—Hydrodeoxygenation and Isomerisation of the Ketone Stream

The resulting ketone stream was hydrodeoxygenated over a $NiMo/Al_2O_3$ catalyst at a temperature of about 310° C., a pressure of about 40 bar, a WHSV of about 1.5 h⁻¹, and $H_2$/feed oil ratio of 900 nl/l to yield a hydrodeoxygenated product. The efficiency of oxygen removal was 99.9% for the HDO step.

The resulting hydrodeoxygenated product was hydroisomerised over a reduced Pt molecular sieve/$Al_2O_3$ as the hydroisomerisation catalyst with at temperature of about 350° C., a pressure of about 40 bar, and at a WHSV of about 1.0 h⁻¹ to yield a hydroisomerised base oil product.

The hydroisomerised base oil product is fractionated into a naphtha fraction (below 180° C.), a diesel fraction (180-350° C.), and the 380+° C. fraction was isolated as a renewable base oil product.

Example 3a—Hydrodeoxygenation and Isomerisation of the Ketone Stream

The resulting ketone stream was hydrodeoxygenated over a $NiMo/Al_2O_3$ catalyst at a temperature of about 310° C., a pressure of about 50 bar, a WHSV of about 1.5 h⁻¹, and $H_2$/feed oil ratio of 900 nl/l to yield a hydrodeoxygenated product. The efficiency of oxygen removal was 99.9% for the HDO step.

The resulting hydrodeoxygenated product was hydroisomerised over Pt/SAPO-11 on alumina support as the hydroisomerisation catalyst with a temperature of about 348° C., a pressure of about 40 bar, at a WHSV of about 1.0 h$^{-1}$, and H$_2$/feed oil ratio of 800 nl/l oil to yield a hydroisomerised base oil product.

The hydroisomerised base oil product is fractionated into a naphtha fraction (below 180° C.), a diesel fraction (180-350° C.), and the 380+° C. fraction was isolated as a renewable base oil product (59.9 wt %), renewable diesel (22.9 wt %), renewable naphtha boiling in the range of 35-180° C. (1.3 wt %) the remainder being product gasses (11.9 wt %) and process oil boiling between 350-380° C. (4.0 wt %).

The renewable base oil product had the following properties: Kinematic viscosity at 40° C. of 17.7 mm$^2$/s; Kinematic viscosity at 100° C. of 4.2 mm$^2$/s; a viscosity index (VI) of 151; cloud point of −1.1° C.; pour point of −17° C.; and aromatics content below 0.1 wt %. The kinematic viscosities measured using ENISO3104, Viscosity index using ASTM D 2270; cloud point using ASTM D 5771; and pour point using ASTM D 5950; aromatic compounds using ASTM D 7419.

Example 4—Hydrodeoxygenation and Isomerisation of the Remaining Palmitic Acid Depleted Stream The remaining palmitic acid depleted feed was hydrodeoxygenated over a NiMo/Al$_2$O$_3$ catalyst at a temperature of about 310° C., a pressure of about 50 bar, a WHSV of about 1.0-1.5 h$^{-1}$, and H$_2$/feed oil ratio of 900 nl/l to yield a hydrodeoxygenated product. The efficiency of oxygen removal was 99.9% for the HDO step.

The resulting hydrodeoxygenated product was hydroisomerised over a platinum impregnated zeolite as the hydroisomerisation catalyst with at temperatures of about 300-350° C., a pressure of about 20-40 bar, and at a WHSV of about 0.8-1.0 h$^{-1}$ to yield a hydroisomerised base oil product.

The hydroisomerised diesel product is fractionated into a naphtha fraction (below 180° C.), a diesel fraction (180-350° C.).

Example 5—Comparison of Ketonisation Catalysts: Production of Trimers

The process of examples 1-4 was repeated with two different ketonisation catalysts.

The palmitic acid feed was fed to a fixed bed reactor operated in continuous mode comprising a catalyst bed loaded with 20 g catalyst material selected as follows for comparison:

1) TiO$_2$ BET 52 m$^2$/g; average pore size 119 Å; crystallinity 94%

2) K$_2$O/TiO$_2$ BET 51 m$^2$/g; average pore size 169 Å; crystallinity 96%

K$_2$O/TiO$_2$ is the ketonisation catalyst used according to the method disclosed in WO 2016/062868 A1.

The ketonisatisation was conducted in the liquid phase at a pressure of about 17.5 bar, a temperature of about 360° C., a CO$_2$ flow of 7.6 l/h, and a WHSV of about 0.6 h$^{-1}$. The ketonisation reaction was run to 99.7-99.8% fatty acid conversion, and the ketone heavy formation was measured.

The ketone heavy formation was about 2.1% when the TiO$_2$ was used, whereas it was about 11.9% when the K$_2$O/TiO$_2$ was used. Thus, a very convincing improvement in relation to production of trimers is obtained with the present catalyst in comparison with the prior art catalyst.

Example 6—Comparison of Metal Leaching

The metal leaching, in a 10 months test run, during the first 3-4 weeks from operation start of the plant was also measured for the two catalysts referred to in example 5. The metal leaching when the TiO$_2$ was used is shown in the table 2:

TABLE 2

| | | L-reactor | | | |
|---|---|---|---|---|---|
| | | Keto product | Keto product catalyst age Days | Keto product | Keto Product |
| Sample | | 1.1 | 4.7 | 11.4 | 16.1 |
| | g feed/g cat | 30.2 | 125.5 | 301.6 | 425.8 |
| ICP-Fe | mg/kg (ppm) | 2.00 | 059 | 0.40 | 0.35 |
| ICP-K | mg/kg (ppm) | 1.00 | 0.47 | 0.30 | 0.25 |
| ICP-Mg | mg/kg (ppm) | 0.30 | 0.00 | 0.00 | 0.00 |
| ICP-Mn | mg/kg (ppm) | 0.00 | 0.00 | 0.00 | 0.00 |
| ICP-Mo | mg/kg (ppm) | 0.33 | 0.11 | 0.05 | 0.05 |
| ICP-Na | mg/kg (ppm) | 1.00 | 0.50 | 0.40 | 0.10 |
| ICP-Zn | mg/kg (ppm) | 0.10 | 0.00 | 0.00 | 0.00 |
| ICP-Ca | mg/kg (ppm) | 0.70 | 0.50 | 0.30 | 0.22 |
| ICP-Cu | mg/kg (ppm) | 0.0 | 0.00 | 0.00 | 0.00 |
| ICP-SI | mg/kg (ppm) | 0.33 | 0.10 | 0.05 | 0.05 |
| Total | mg/kg (ppm) | 6.55 | 2.52 | 1.55 | 1.05 |

In comparison, the metal leaching when the K$_2$O/TiO$_2$ was used is shown in table 3:

TABLE 3

| | Days | Ketone product 1.1 | Ketone product 4.8 | Ketone product 8.5 | Ketone product 13.1 | Ketone product 15.9 | Ketone product 31.6 |
|---|---|---|---|---|---|---|---|
| Catalyst age | gfeed/gcat | 30.1 | 127.2 | 225.7 | 344.6 | 418.6 | 833.4 |
| ICP-Fe | mg/kg (ppm) | 3.70 | 1.70 | 1.60 | 1.40 | 1.40 | 0.03 |
| ICP-K | mg/kg (ppm) | 75.00 | 12.00 | 5.60 | 2.90 | 2.20 | 0.13 |
| ICP-Mg | mg/kg (ppm) | 2.00 | 0.39 | 0.37 | 0.33 | 0.31 | 0.02 |
| ICP-Mn | mg/kg (ppm) | 0.04 | 0.01 | 0.00 | 0.00 | 0.00 | 0.00 |
| ICP-Mo | mg/kg (ppm) | 0.13 | 0.06 | 0.10 | 0.19 | 0.14 | 0.02 |
| ICP-Na | mg/kg (ppm) | 150.00 | 40.00 | 19.00 | 14.00 | 12.00 | 2.50 |
| ICP-Zn | mg/kg (ppm) | 0.34 | 0.00 | 0.43 | 0.24 | 0.28 | 0.00 |
| ICP-Ca | mg/kg (ppm) | 7.00 | 1.50 | 1.20 | 1.10 | 1.00 | 0.19 |
| ICP-Cu | mg/kg (ppm) | 0.07 | 0.04 | 0.04 | 0.04 | 0.05 | 0.00 |
| ICP-Si | mg/kg (ppm) | 0.28 | 0.08 | 0.14 | 0.10 | 0.27 | 0.00 |
| Total | mg/kg (ppm) | 238.69 | 55.87 | 28.57 | 20.33 | 17.69 | 2.88 |

Feed metals, in particular within the first 3-4 weeks of the run, should preferable be less than 10 ppm, such as less than 5 ppm, e.g. less than 3 ppm, in order to minimise the fouling and deactivation of subsequent HDO reactor. The full leaching of potassium during 3-4 weeks can totally deteriorate the activity of HDO catalyst or give rise to unbearably pressure drop of the catalyst bed.

Thus, it is apparent that the $TiO_2$ catalyst fulfils this criterion, whereas the $K_2O/TiO_2$ does not. In particular the leaching of potassium, sodium and calcium is minimised to a beneficial level with the $TiO_2$ catalyst in comparison with the leaching of these metals from the $K_2O/TiO_2$.

The invention claimed is:

1. A method for producing renewable base oil and diesel fuel from a feedstock of biological origin, the method comprising:
   a) providing a feedstock, the feedstock including 2-95 wt % of a mixture of free fatty acids; 5-98 wt % fatty acid glycerols selected from mono-glycerides, di-glycerides and tri-glycerides of fatty acids; 0-50 wt % of one or more compounds selected from a list consisting of: fatty acid esters of the non-glycerol origin, fatty amides and fatty alcohols; wherein at least 50 wt % of the feedstock is a mixture of free fatty acids and fatty acid glycerols; and separating the feedstock from step a) into at least the following two feeds:
   a1) a free fatty acid enriched feed which has a higher concentration of free fatty acids than the feedstock and wherein the free fatty acids include $C_{10}$-$C_{24}$ fatty acids; and
   a2) one or more free fatty acid depleted feed(s) which has a higher concentration of compounds selected from mono-glycerides, di-glycerides, and tri-glycerides of fatty acids, and a higher boiling point than the free fatty acid enriched feed;
   b) subjecting the free fatty acid enriched feed to ketonisation under ketonisation reaction conditions in a presence of a ketonisation catalyst selected as metal oxide catalyst essentially containing titanium as the metal, where a content of an element potassium is 0.05 wt % or less, and where two free fatty acids react to yield a ketone stream, the ketone stream containing as a major part saturated ketones;
   c) subjecting the ketone stream to both hydrodeoxygenation under hydrodeoxygenation reaction conditions and to hydroisomerisation under hydroisomerisation reaction conditions, simultaneously or in sequence, to yield a deoxygenated and isomerised base oil product stream containing the renewable base oil; and
   d) transforming the one or more free fatty acid depleted feed(s) into a diesel product by subjecting the one or more free fatty acid depleted feed(s) to both hydrodeoxygenation under hydrodeoxygenation reaction conditions and to hydroisomerisation under hydroisomerisation reaction conditions, simultaneously or in sequence, to yield a deoxygenated and isomerised diesel product stream containing the diesel fuel.

2. The method according to claim 1, wherein the ketonisation catalyst is $TiO_2$ on a support.

3. The method according to claim 1, wherein the ketonisation catalyst comprises a content of elements manganese, magnesium, calcium and potassium that is 0.05 wt % or less compared to a total catalyst weight.

4. The method according to claim 2, wherein the $TiO_2$ is in anatase form having an average pore diameter of 80-160 Å, and/or a BET area of 20-140 $m^2/g$, and/or a porosity of 0.1-0.3 $cm^3/g$.

5. The method according to claim 1, wherein the ketonisation reaction conditions comprise at least one of:
   conducting ketonisation at a temperature in a range of 300 to 400° C.;
   conducting ketonisation at a pressure in a range of 5 to 30 barg;
   conducting ketonisation at a WHSV (Weight Hourly Space Velocity) in a range of 0.25 to 3 $h^{-1}$; and
   conducting ketonisation in a presence of a gas, wherein the gas is selected from one or more of $CO_2$, $H_2$, $N_2$, $CH_4$, and $H_2O$, in a range of 0.1 to 1.5 gas/feed ratio (w/w).

6. The method according to claim 1, wherein the ketonisation is conducted at least partly in liquid form.

7. The method according to claim 1, comprising:
   distilling the deoxygenated and isomerised base oil product stream containing the renewable base oil to obtain distilled renewable base oil.

8. The method according to claim 1, comprising:
   distilling the deoxygenated and isomerised diesel product stream containing the diesel fuel to obtain distilled diesel fuel.

9. The method according to claim 1, comprising:
   producing a naphtha fuel, where the naphtha fuel is obtained from distillation of the deoxygenated and isomerised base oil product stream containing the renewable base oil and/or the deoxygenated and isomerised diesel product stream containing the diesel fuel.

10. The method according to claim 1, comprising:
    pre-treating prior to step a), an initial feedstock containing fatty acid esters in at least a hydrolysis step thereby producing the feedstock, wherein a ratio of free fatty acids to fatty acid esters in the feedstock has been increased compared to the initial feedstock.

11. The method according to claim 1, wherein no pre-treatment by hydrogenation or by hydrolysis is made in or in-between any of the steps a), a1), a2), and b).

12. The method according to claim 1, where the hydrodeoxygenation and hydroisomerisation of the ketone stream take place in sequence, and where in-between the hydrodeoxygenation and hydroisomerisation there is a stripping step, where gasses are separated from liquids in a high temperature and high pressure separation step, at a temperature in a range from 300 to 330° C., and/or at a pressure in a range from 40 to 50 barg.

13. The method according to claim 7, wherein prior to the distillation step of the deoxygenated and isomerised base oil product stream containing the renewable base oil, the method comprises:
    a stripping step, where gases are separated from liquids, and/or at a pressure in a range from 3 to 6 barg.

14. The method according to claim 1, wherein at least one of the following conditions is satisfied:
    the feedstock or the free fatty acid enriched feed mainly contains at least one of saturated fatty acids and $C_{16}$ fatty acids; and
    the feedstock is palm oil fatty acid distillate (PFAD).

15. The method according to claim 1, wherein at least one of the following conditions is satisfied:
    the ketonisation catalyst is $TiO_2$, and wherein a content of metal impurities in the feedstock or the free fatty acid enriched feed immediately before it is subjected to the ketonisation reaction conditions and in the ketone stream obtained immediately after it has been subjected to the ketonisation reaction conditions contains at most 20 ppm manganese, at most 20 ppm magnesium, at most 20 ppm calcium, and at most 20 ppm potassium, measured using inductively coupled plasma (ICP) metal analysis; and the ketone stream obtained immediately after the free fatty acid enriched feed has been subjected to the ketonisation reaction conditions contains at most 5 ppm manganese, at most 5 ppm calcium, and at most 5 ppm potassium, measured using inductively coupled plasma (ICP) metal analysis.

16. The method according to claim 1, where the ketone stream obtained immediately after the free fatty acid enriched feed has been subjected to the ketonisation reaction conditions contains at most 3 ppm manganese, at most 3 ppm calcium, and at most 3 ppm potassium, measured using inductively coupled plasma (ICP) metal analysis.

17. The method according to claim 1, wherein the hydrodeoxygenation reaction conditions include at least one of a temperature in a range from 250 to 400° C., a pressure in a range from 20 to 80 barg, a WHSV in a range from 0.5-3 $h^{-1}$, and a $H_2$ flow of 350-900 nl $H_2$/l feed, in a presence of a hydrodeoxygenation catalyst, or NiMo on an alumina support.

18. The method according to claim 1, wherein the hydroisomerisation reaction conditions include at least one of a temperature in a range from 250 to 400° C., a pressure in a range from 10 to 60 barg, a WHSV in a range from 0.5-3 $h^{-1}$, and a $H_2$ flow of 100-800 nl $H_2$/l feed, in a presence of an isomerisation catalyst, or a catalyst containing a Group VIII metal and a molecular sieve, on an alumina and/or silica support.

19. The method according to claim 1, wherein the hydrodeoxygenation and hydroisomerisation reaction conditions include a catalyst that is the same.

20. The method according to claim 1, wherein at least 50 wt % of the feedstock is the mixture of free fatty acids and fatty acid glycerols.

21. The method according to claim 1, wherein the renewable base oil is a hydrocarbon composition having a viscosity index of at least 80, or the renewable base oil fulfils requirements for sulfur, saturates and viscosity index of API (the American Petroleum Institute) group I, II or III.

22. The method according to claim 1, wherein at least 70 wt % of the feedstock is a mixture of free fatty acids and fatty acid glycerols.

23. The method according to claim 1, wherein the feedstock comprises at least one of:
at least 10 wt % free fatty acids;
90 wt % free fatty acids or less; and
from 10 to 90 wt % free fatty acids.

24. The method according to claim 1, wherein the feedstock comprises at least one of:
at least 10 wt % fatty acid glycerols;
90 wt % fatty acid glycerols or less; and
from 10 to 90 wt % fatty acid glycerols.

25. The method according to claim 1, wherein the feedstock is selected to comprise at least one of:
at least 10% of one or more compounds selected from a list consisting of: fatty acid esters of the non-glycerol type, fatty amides and fatty alcohols;
from 15 to 45%, from 20 to 40%, or from 25 to 35% of one or more compounds selected from a list consisting of: fatty acid esters of the non-glycerol type, fatty amides, and fatty alcohols; and
from 10 to 50%, from 15 to 45%, from 20 to 40%, or from 25 to 35% of fatty acid esters of a non-glycerol origin.

26. The method according to claim 1, wherein the method further comprising:
selecting a ketonisation catalyst as a metal oxide catalyst essentially containing titanium as metal, where a content of an element potassium is 0.05 wt % or less, for improving catalyst life time of a hydrodeoxygenation catalyst in a plant for producing renewable diesel and/or base oil, the plant including a fatty acid ketonisation stage containing a ketonisation catalyst; the plant including a hydrodeoxygenation stage having a hydrodeoxygenation catalyst; the hydrodeoxygenation stage being downstream of the ketonisation stage.

27. The method according to claim 26, wherein the ketonisation catalyst consists essentially of:
$TiO_2$ on a support, and where a content of elements manganese, magnesium, calcium and potassium is 0.05 wt % or less compared to a total catalyst weight.

28. The method according to claim 26, wherein the ketonisation catalyst consists essentially of:
$TiO_2$ on a support, and where a content of the element potassium is 0.05 wt % or less compared to a total catalyst weight.

29. The method according to claim 26, wherein the fatty acid ketonisation stage comprises:
fatty acids selected from $C_{12}$-$C_{22}$ fatty acids.

30. The method according to claim 26, wherein the hydrodeoxygenation stage comprises:
ketones selected from $C_{23}$-$C_{43}$ ketones.

* * * * *